United States Patent
Pohl et al.

(10) Patent No.: US 10,723,885 B2
(45) Date of Patent: Jul. 28, 2020

(54) PROCESS FOR IMPROVING PARTICLE SIZE DISTRIBUTION OF CALCIUM CARBONATE-COMPRISING MATERIAL

(71) Applicant: Omya International AG, Oftringen (CH)

(72) Inventors: Michael Pohl, Villach (AT); Christian Rainer, Villach (AT); Martin Brunner, Wallbach (CH); Jürgen Spehn, Safenwil (CH); Michael Tinkl, Gipf-Oberfrick (CH); Dennis Werner, Olten (CH); Armelle Senti-Wenk, Wettingen (CH); Emmanuel Goutard, Les Taillades (FR)

(73) Assignee: OMYA INTERNATIONAL AG, Oftringen (CH)

( * ) Notice: Subject to any disclaimer, the term of this patent is extended or adjusted under 35 U.S.C. 154(b) by 0 days.

(21) Appl. No.: 15/512,689

(22) PCT Filed: Sep. 28, 2015

(86) PCT No.: PCT/EP2015/072275
§ 371 (c)(1),
(2) Date: Mar. 20, 2017

(87) PCT Pub. No.: WO2016/050698
PCT Pub. Date: Apr. 7, 2016

(65) Prior Publication Data
US 2017/0283619 A1 Oct. 5, 2017

Related U.S. Application Data

(60) Provisional application No. 62/134,283, filed on Mar. 17, 2015, provisional application No. 62/061,218, filed on Oct. 8, 2014.

(30) Foreign Application Priority Data

Sep. 30, 2014 (EP) .................................... 14186967

(51) Int. Cl.
| | | |
|---|---|---|
| C09C 1/02 | (2006.01) |
| A61K 8/19 | (2006.01) |
| D21H 19/38 | (2006.01) |
| C09D 1/00 | (2006.01) |
| C01F 11/18 | (2006.01) |
| C09D 5/00 | (2006.01) |
| D21H 21/52 | (2006.01) |
| D21H 17/67 | (2006.01) |
| A61Q 19/00 | (2006.01) |
| A61K 8/02 | (2006.01) |
| C08K 3/26 | (2006.01) |
| C08K 9/10 | (2006.01) |
| C09J 11/04 | (2006.01) |

(52) U.S. Cl.
CPC ............ *C09C 1/022* (2013.01); *A61K 8/0208* (2013.01); *A61K 8/0241* (2013.01); *A61K 8/19* (2013.01); *A61Q 19/00* (2013.01); *C01F 11/185* (2013.01); *C08K 3/26* (2013.01); *C08K 9/10* (2013.01); *C09C 1/021* (2013.01); *C09D 1/00* (2013.01); *C09D 5/00* (2013.01); *C09J 11/04* (2013.01); *D21H 17/675* (2013.01); *D21H 19/385* (2013.01); *D21H 21/52* (2013.01); *A61K 2800/10* (2013.01); *A61K 2800/412* (2013.01); *C01P 2004/51* (2013.01); *C01P 2004/52* (2013.01); *C01P 2004/61* (2013.01); *C01P 2004/62* (2013.01); *C01P 2006/12* (2013.01); *C01P 2006/22* (2013.01); *C01P 2006/60* (2013.01); *C01P 2006/62* (2013.01); *C01P 2006/63* (2013.01); *C01P 2006/64* (2013.01); *C08K 2003/265* (2013.01)

(58) Field of Classification Search
CPC ...................................................... C09C 1/022
See application file for complete search history.

(56) References Cited

U.S. PATENT DOCUMENTS

| | | |
|---|---|---|
| 5,269,818 A | 12/1993 | Kunesh et al. |
| 5,296,002 A | 3/1994 | Passaretti |
| 2002/0155055 A1 | 10/2002 | Denholm et al. |

(Continued)

FOREIGN PATENT DOCUMENTS

| | | |
|---|---|---|
| CN | 1161996 A | 10/1997 |
| EP | 0447094 A1 | 3/1991 |

(Continued)

OTHER PUBLICATIONS

International Search Report dated Nov. 25, 2015 for PCT/EP2015/072275.

(Continued)

Primary Examiner — Stuart L Hendrickson
(74) Attorney, Agent, or Firm — Fay Sharpe LLP

(57) ABSTRACT

The present invention relates to a process for the preparation of an aqueous suspension comprising at least one calcium carbonate-comprising material, the calcium carbonate-comprising material having a ratio of particles having an average particle size $d_{80}$ value to particles having an average particle size $d_{20}$ value [$d_{80}/d_{20}$] in the range from 1.5 to 4 and the use of the calcium carbonate-comprising material in paper and board applications, in cosmetics, in caulks and sealants, in adhesives, in paints and coatings, in fibre applications, in plastics applications or for the replacement of PCC in general.

39 Claims, 2 Drawing Sheets

(56) References Cited

U.S. PATENT DOCUMENTS

2010/0074827 A1 3/2010 Rainer et al.
2015/0040800 A1 2/2015 Gane et al.
2016/0264785 A1 9/2016 Pohl et al.

FOREIGN PATENT DOCUMENTS

EP 1764346 A1 3/2007
EP 2644568 A1 10/2013

OTHER PUBLICATIONS

Written Opinion of the International Searching Authority dated Nov. 25, 2015 for PCT/EP2015/072275.
Examination Report dated Aug. 4, 2017 for Australian Application No. 2015327060.
Office action dated Feb. 8, 2018 for Canadian Application No. 2,962,316.
Office action dated Nov. 1, 2017 for Chinese Application No. 201580053199.7.
European Search Report dated Mar. 12, 2015 for European Application No. 14186967.7.
Examination Report dated Mar. 11, 2018 for the Cooperation Council for the Arab States of the Gulf Application No. GC 2015-30107.
Office action dated Mar. 20, 2018 for Japanese Application No. 2017-517243.
Search Report dated Apr. 24, 2018 for Russian Application No. 2017114998.
Decision to Grant dated Apr. 24, 2018 for Russian Application No. 2017114998.
International Preliminary Report on Patentability dated Apr. 13, 2017 for Application No. PCT/EP2015/072275.
Office Action dated Aug. 8, 2018 from U.S. Appl. No. 15/030,422.
Office Action dated Feb. 1, 2019 from Indian Application No. 201727010075.

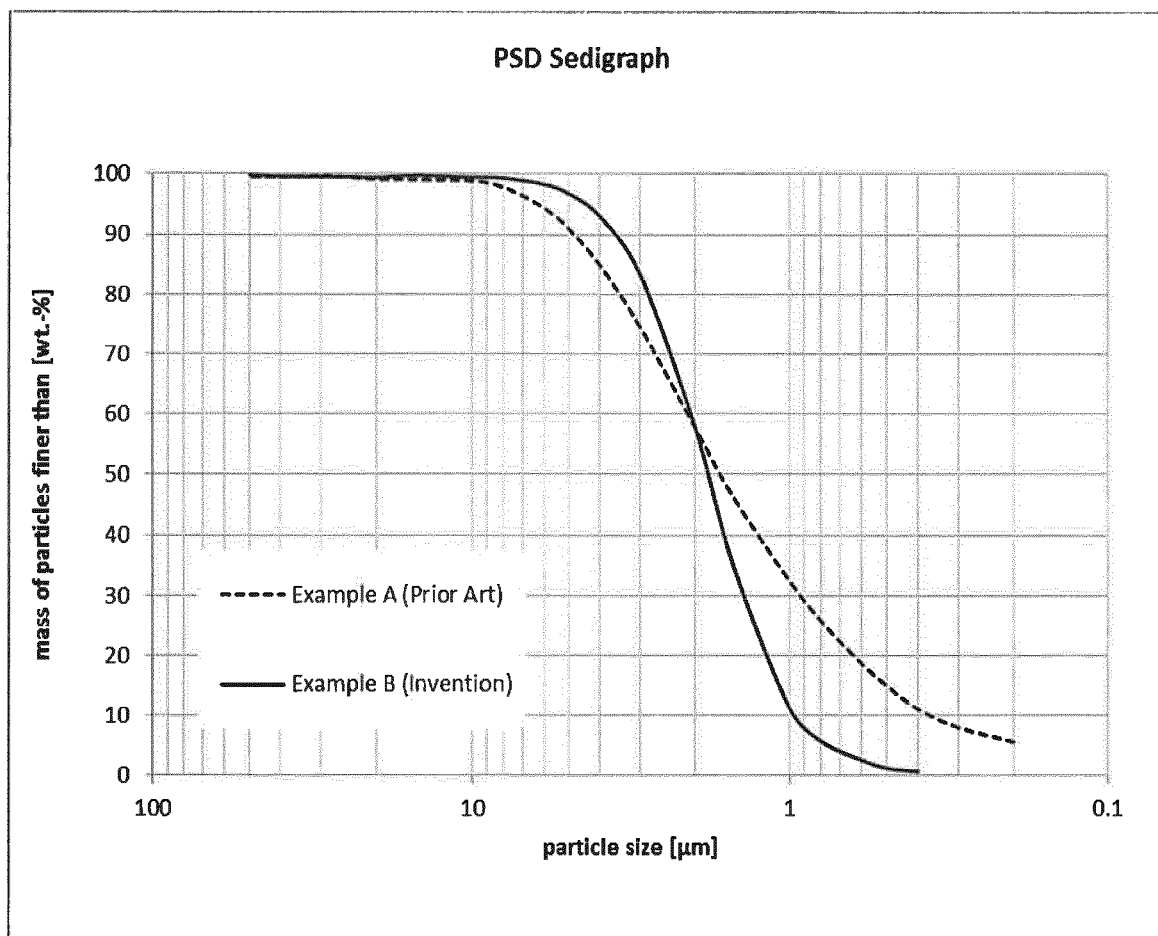
Fig. 1: PSD Sedigraph, examples A-B.

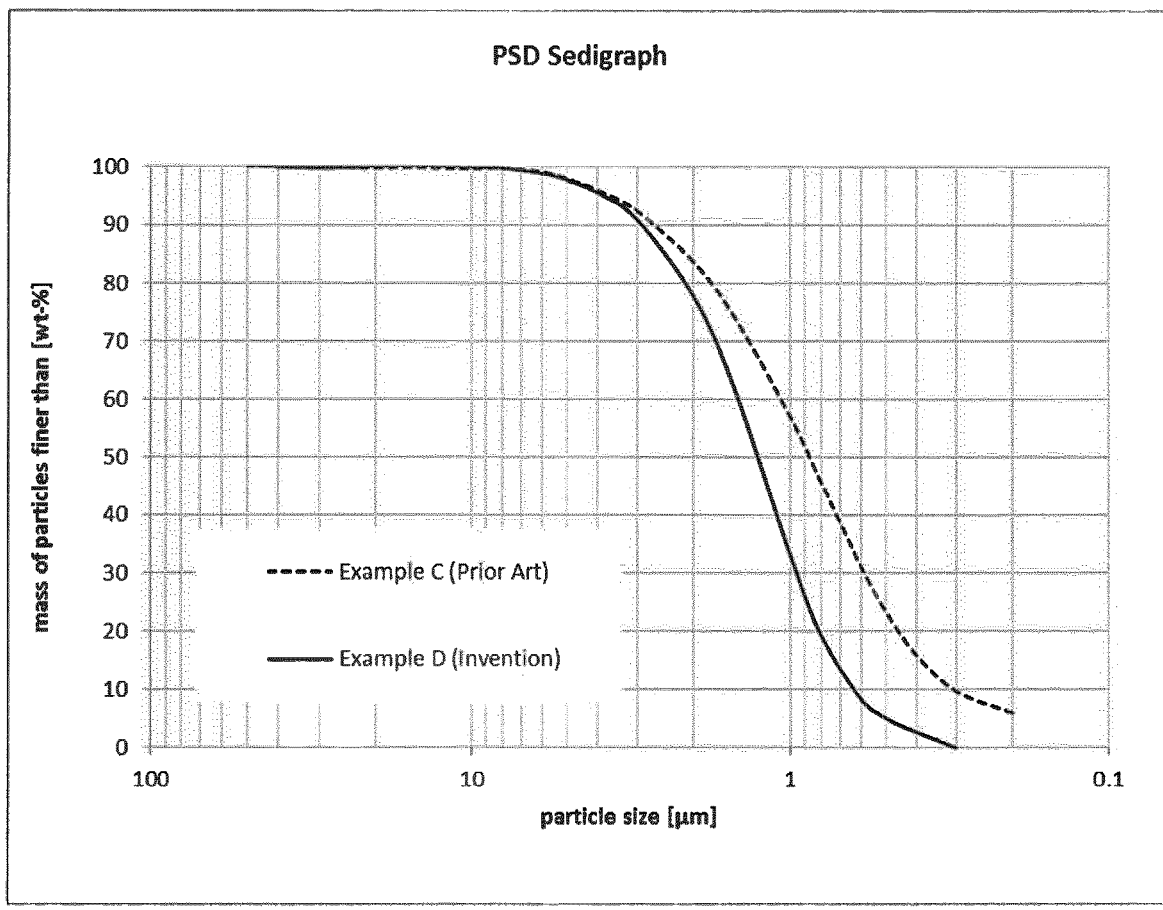
Fig. 2: PSD Sedigraph, examples C-D.

PROCESS FOR IMPROVING PARTICLE SIZE DISTRIBUTION OF CALCIUM CARBONATE-COMPRISING MATERIAL

CROSS-REFERENCE TO RELATED APPLICATIONS

This is a U.S. national phase of PCT Application No. PCT/EP2015/072275, filed Sep. 28, 2015, which claims priority to European Application No. 14186967.7, filed Sep. 30, 2014 and U.S. Provisional Application Nos. 62/061,218, filed Oct. 8, 2014 and 62/134,283, filed Mar. 17, 2015.

The present invention relates to a process for the preparation of an aqueous suspension comprising at least one calcium carbonate-comprising material. The invention further relates to the use of the calcium carbonate-comprising material obtainable by the inventive process in paper and board applications, in cosmetics, in caulks and sealants, in adhesives, in paints and coatings, in fibre applications, in plastics applications or for the replacement of PCC (=precipitated calcium carbonate) in general.

Calcium carbonate is used extensively in the paper industry as a filler component in paper. It is a low cost, high brightness filler used to increase sheet brightness and opacity. Its use has increased dramatically in the last decades due to the conversion from acid to alkaline papermaking at paper mills. Calcium carbonate is known to exist as natural occurring minerals as well as synthetically produced products. Both natural and synthetic calcium carbonates are used in the paper industry. Besides its use in the paper industry, calcium carbonates are also used for various other purposes, e.g. as filler or pigment in the paint industries, and as functional filler for the manufacture of plastic materials, plastisols, sealing compounds, printing inks, rubber, toothpaste, cosmetics, agricultural applications etc.

Natural calcium carbonate is typically ground to a small particle size prior to its use in paper or other applications.

However, for many applications it is desired to provide a calcium carbonate having a low BET specific surface area and narrow particle size distribution at low content of fines as these characteristics typically impart good mechanical and optical properties, like gloss, to a polymer product comprising such calcium carbonate. Furthermore, a narrow particle size distribution at low BET specific surface area is advantageous for hydrophobized calcium carbonate products typically used for plastic applications as the amount of, for example, stearic acid, which may be used as hydrophobizing agent for preparing such hydrophobized products, can be reduced. In addition thereto, said narrow particle size distribution at low BET specific surface area has also positive effects on calcium carbonate slurries as the amount of dispersants often used for dispersing calcium carbonate in the slurry can be reduced.

In this regard, methods for decreasing the BET specific surface area and narrowing the particle size distribution are well known in the art. For example, U.S. Pat. No. 5,269,818 A refers to a heat-aging process which is adapted to produce large amounts of heat-aged calcium carbonate suspension. The process comprises the steps of initiating heat-aging of the calcium carbonate having a specific surface area greater than about 15 m²/g by heating it to an aging temperature of from about 40° C. to about 100° C.; adjusting the pH of the calcium carbonate at the aging temperature to about 6.5, such as by addition of carbon dioxide; adding an alkali metal hydroxide to the calcium carbonate at the aging temperature to raise the pH to from about 9.5 to about 12.0; maintaining the calcium carbonate at the aging temperature for a sufficient time to cause the morphology of the calcium carbonate to rearrange to the final form; and terminating heat-aging to fix the morphology of the calcium carbonate in the final form. US 2002/0155055 A1 relates to ground calcium carbonate compositions having narrow particle size distributions and a method for producing the compositions. The method involves forming a substantially dispersant-free calcium carbonate suspension, wet-grinding the suspension, and aging the suspension. Aging takes place at temperatures below 40° C.

However, these methods have the drawback that such aging processes are typically time-consuming. For example, it is described in U.S. Pat. No. 5,269,818 A that where the calcium carbonate starting material has an initial average particle size of from about 0.01 to about 0.5 µm and has a high purity, the aging time is as short as about 60 minutes, while for a calcium carbonate starting material having a larger initial agglomerated particle size of from about 0.5 to about 2 µm, and/or containing impurities of up to about 5 weight percent, the heat-aging time can be as long as 24 hours. Similar to that US 2002/0155055 A1 describes that aging will last about 24 hours.

Another method for the preparation of a calcium carbonate-comprising material with a narrow particle size distribution is described in an at the time of filing the present application unpublished European patent application (application number: 13192156.1, filed on Nov. 13, 2013) of the same applicant as the present application. Said method comprises the steps a) providing a substantially dispersant-free aqueous suspension of at least one calcium carbonate-comprising material, b) pre-heating the suspension of step a) to a temperature of from 40 to 95° C. at ambient pressure, c) contacting the aqueous suspension of step a) before and/or during and/or after pre-heating step b) with at least one base for obtaining an aqueous suspension having a pH measured at 25° C. of ≥9.0, and d) wet-grinding the pre-heated suspension of step b) or of step c) in at least one grinding step for obtaining an aqueous suspension of at least one calcium carbonate-comprising material having a ratio of particles having an average particle size $d_{80}$ value to particles having an average particle size $d_{20}$ value $[d_{80}/d_{20}]$ of ≤2.50.

There is still a need in the art for providing alternative processes for preparing a calcium carbonate-comprising material having a narrow particle size distribution, a low moisture pick-up susceptibility and low BET specific surface area, wherein such process should be simple and inexpensive, not strongly limited in view of the coarseness of the starting material while avoiding the use of time-consuming ageing steps after grinding, or at least reducing the ageing time.

Accordingly, it is an objective of the present invention to provide an improved process for preparing a calcium carbonate-comprising material having an improved or optimized narrow particle size distribution at a low amount of fines. Another objective of the present invention may be seen in the provision of a process for preparing a calcium carbonate-comprising material having reduced or optimized values for the BET specific surface area. A further objective of the present invention may be seen in the provision of a process for preparing a calcium carbonate-comprising material having improved or optimized optical properties such as opacity and brightness and light scattering properties and mechanical properties. Another objective of the present invention may be seen in the provision of a process for preparing a calcium carbonate-comprising material being available as partially dewatered or dried calcium carbonate-comprising material. Even a further objective of the present invention may be seen in the provision of a process for preparing wet-ground calcium carbonate which can be carried out in a simple and inexpensive way. Another objective of the present invention may be seen in the provision of a process not strongly limited in view of the coarseness of the starting material. Further objectives can be gathered from the following description of the invention.

In order to fulfil the foregoing need(s) a process according to the subject-matter as defined herein in claim 1 is provided.

Advantageous embodiments of the inventive process are defined in the corresponding sub-claims and the specification.

According to one aspect of the present invention a process for the preparation of an aqueous suspension comprising at least one calcium carbonate-comprising material, the process comprising the following steps:
 a) providing a substantially dispersant-free aqueous suspension of at least one calcium carbonate-comprising material, and
 b) pre-heating the suspension of step a) to a temperature of from 40 to 95° C. at ambient pressure, and
 c) wet-grinding the pre-heated suspension in at least one grinding step for obtaining an aqueous suspension of at least one wet ground calcium carbonate-comprising material, and
 d) contacting the aqueous suspension before and/or during and/or after wet-grinding step c) and/or before and/or during and/or after removal step e) with at least one base for obtaining an aqueous suspension having a pH measured at 25° C. of ≥9.0, and
 e) removal of at least a part of the particles with a diameter >20 μm in the aqueous suspension of the at least one wet ground calcium carbonate comprising material, and
 f) storing the aqueous suspension obtained after removal step e) at a temperature of from 70 to 140° C. for a period of time of 0.25 to 8 hours, for obtaining an aqueous suspension of at least one calcium carbonate-comprising material having a ratio of particles having an average particle size $d_{80}$ value to particles having an average particle size $d_{20}$ value $[d_{80}/d_{20}]$ in the range from 1.5 to 4.0.

The inventors surprisingly found out that the foregoing process allows for the efficient and controlled production of a calcium carbonate-comprising material having an improved or optimized narrow particle size distribution at a low amount of fines, as well as improved or optimized BET specific surface area. According to the process of the present invention a calcium carbonate-comprising material having improved or optimized optical properties and light scattering properties as well as mechanical properties can be prepared directly in a simple and inexpensive way. The calcium carbonate-comprising material obtainable by the inventive process also was found to be especially suitable for the application in plastics due to its good mechanical properties. More precisely, the inventors found out that the particle size distribution as well as the BET specific surface area of a calcium carbonate-comprising material being obtained by said process can be improved or optimized by specifically grinding a pre-heated suspension of a calcium carbonate-comprising material featuring a pH of ≥9.0. Further essential steps of the inventive process refer to a partial removal of very coarse particles and the specified ripening or storing step.

It should be understood that for the purposes of the present invention, the following terms have the following meanings:

A "suspension" or "slurry" in the meaning of the present invention comprises insoluble solids and water and optionally further additives and usually contains large amounts of solids and, thus, is more viscous and generally of higher density than the liquid from which it is formed.

The term "calcium carbonate-comprising material" in the meaning of the present invention comprises at least 40.0 wt.-% calcium carbonate, based on the total dry weight of the calcium carbonate-comprising material. Preferably, the calcium carbonate-comprising material comprises at least 60.0 wt.-%, more preferably at least 80.0 wt.-%, even more preferably at least 85.0 wt.-%, even more preferably at least 90.0 wt.-% and most preferably at least 95.0 wt.-%, such as at least 98.0 wt.-%, of calcium carbonate, based on the total dry weight of the calcium carbonate-comprising material.

The "moisture pick up susceptibility" of a material refers to the amount of moisture absorbed on the surface of said material within a certain time upon exposure to a defined humid atmosphere and is expressed in mg/g. The "normalized moisture pick up susceptibility" of a material also refers to the amount of moisture absorbed on the surface of said material within a certain time upon exposure to a defined humid atmosphere and is expressed in $mg/m^2$. The moisture pick up susceptibility can be determined in mg moisture/g after exposure to an atmosphere of 10 and 85% relative humidity, respectively, for each 2.5 h at a temperature of +23° C. (±2° C.). For this purpose, the sample is first kept at an atmosphere of 10% relative humidity for 2.5 h, then the atmosphere is changed to 85% relative humidity at which the sample is kept for another 2.5 hours. The weight increase between 10 and 85% relative humidity is then used to calculate the moisture pick-up in mg moisture/g of sample. The moisture pick up susceptibility in mg/g divided by the specific surface area in $m^2$ (BET method) corresponds to the normalized moisture pick up susceptibility expressed in $mg/m^2$ of sample.

As used herein and as generally defined in the art, the "$d_{80}$" value and "$d_{20}$" value are determined based on measurements made by using a Sedigraph™ III Plus of Micromeritics Instrument Corporation (operating instrument software version 1.04) and is defined as the size at which 80% and 20%, respectively, of the particle mass is accounted for by particles having a diameter finer than or equal to the specified value. Analogical, the $d_{50}$ value is thus the "weight median particle size" at which 50 wt.-% of all particles are smaller than the indicated particle size. The method and the instrument are known to the skilled person and are commonly used to determine grain size of fillers and pigments. For example, particle sizes defined within the present application being smaller than 20 μm can be determined based on measurements made by using a Sedigraph™ III Plus of Micromeritics Instrument Corporation (operating instrument software version 1.04). The method and the instrument are known to the skilled person and are commonly used to determine the particle size of fillers and pigments. In case of particle sizes being 20 μm or larger, fractional sieving or wet screening is used to determine particle size distributions.

The term "base" in the meaning of the present invention refers to a base in accordance with the Brønsted-Lowry concept.

The expression "ambient pressure" in the meaning of the present invention may refer to pressures between 1000 and 1050 mbar.

The expression "wet ground calcium carbonate-comprising material" in the meaning of the present invention refers to every calcium carbonate-comprising material which has been manufactured by a process including at least one grinding step in an aqueous suspension, wherein the solid content is between 20 and 80 wt.-% for GCC and between 2 and 98 wt.-% for nanoproducts or for PCC.

Where the term "comprising" is used in the present description and claims, it does not exclude other elements. For the purposes of the present invention, the expression "consisting of" is considered to be a preferred embodiment of the expression "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless otherwise specifically stated.

Terms such as "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

According to second aspect, the present invention refers to the use of the calcium carbonate comprising material obtainable by the inventive process in paper and board applications, in cosmetics, in caulks and sealants, in adhesives, in paints and coatings, in fibre applications, in plastics applications or for the replacement of PCC in general. A more detailed list of preferred uses is given below.

It is to be understood that the following preferred embodiments relating to the inventive process of the first aspect also apply to the inventive use as claimed. Furthermore, the following preferred embodiments can be combined with each other according to the present invention.

According to one embodiment of the inventive process, the content of particles with a particle diameter <1 µm of the at least one calcium carbonate-comprising material provided in the aqueous suspension of step a) is between 30 to 90 wt.-%, preferably between 35 and 65 wt.-% and most preferably between 40 and 60 wt.-%, based on the weight of the at least one calcium carbonate-comprising material. The inventive process is especially suitable for the processing of relatively coarse starting materials. According to another embodiment of the inventive process, the at least one calcium carbonate-comprising material provided in the aqueous suspension of step a) is dolomite and/or a natural ground calcium carbonate (NGCC), such as one or more of marble, limestone and/or chalk.

According to another embodiment of the inventive process, the aqueous suspension provided in step a) has a solids content of from 5.0 wt.-% to 60.0 wt.-%, preferably from 10.0 wt.-% to 55.0 wt.-% and most preferably from 15.0 wt.-% to 50.0 wt.-%, based on the total weight of the aqueous suspension.

According to yet another embodiment of the inventive process, the aqueous suspension of step a) is adjusted in pre-heating step b) to a temperature of from 50 to 95° C. at ambient pressure, preferably from 60 to 90° C. at ambient pressure and more preferably from 75 to 85° C. at ambient pressure.

The contacting step d) according to a preferred embodiment of the inventive process is carried out after removal step e).

According to another embodiment of the inventive process, the contacting step d) is carried out such that the obtained aqueous suspension has a pH measured at 25° C. of from 10.0 to 13.5 and preferably from 11.0 to 13.0.

According to another embodiment of the inventive process, the at least one base in contacting step d) is a) added in an amount of ≥0.05 wt.-%, preferably of ≥0.1 wt.-%, more preferably of ≥0.2 wt.-% and most preferably of from 0.2 to 1.0 wt.-%, based on the total dry weight of the calcium carbonate-comprising material, and/or b) at least one alkali metal hydroxide selected from the group comprising lithium hydroxide, sodium hydroxide, potassium hydroxide and mixtures thereof and/or at least one earth alkali metal hydroxide selected from the group comprising magnesium hydroxide, calcium hydroxide and mixtures thereof.

According to yet another embodiment of the inventive process, the wet-grinding step c) is carried out at a starting temperature of from 40 to 95° C., preferably from 60 to 80° C., more preferably from 65 to 75° C.

It is furthermore preferred according to the inventive process that the removal step e) is carried out by using a centrifuge, at least one sieve or a disc separator or mixtures thereof for removing >90 wt.-% of particles with a diameter >100 µm and >70 wt.-% of particles with a diameter >20 µm, preferably for removing essentially all particles with a diameter >100 µm and >90 wt.-% of particles with a diameter >20 µm, based on the weight of at least one wet ground calcium carbonate comprising material.

According to yet another embodiment of the inventive process, step f) of storing the aqueous suspension is carried out at a temperature of from 75 to 130° C. and most preferably from 80 to 95° C., and/or for a period of time of 0.1 to 7 hours, preferably 0.5 to 3.5 hours, more preferably 0.75 to 2.5 hours and most preferably 1 to 2 hours.

According to another embodiment of the inventive process, the aqueous suspension stored in step f) has solids content of from 5.0 wt.-% to 60.0 wt.-%, preferably from 10.0 wt.-% to 55.0 wt.-%, more preferably from 15.0 wt.-% to 50.0 wt.-% and most preferably from 20.0 wt.-% to 50.0 wt.-%, based on the total weight of the aqueous suspension.

It is furthermore preferred according to the inventive process that the ratio of particles having an average particle size $d_{80}$ value to particles having an average particle size $d_{20}$ value $[d_{80}/d_{20}]$ of the at least one calcium carbonate-comprising material obtained after storing step f) is in the range from 1.7 to 3.5, preferably from 2.2 to 3.4.

According to yet another embodiment of the inventive process, the process further comprises step g) of dewatering and optionally drying the aqueous suspension obtained in step e) or f) to remove at least a portion of water to obtain a partially dewatered calcium carbonate-comprising material or to obtain a dried calcium carbonate-comprising material.

According to still another embodiment of the inventive process water, preferably deionised water, is added to the partially dewatered calcium carbonate-comprising material obtained after step g) or to the dried calcium carbonate-comprising material to obtain an aqueous suspension and the obtained aqueous suspension is dewatered, preferably mechanically, again, preferably the procedure of adding water and dewatering is repeated two times.

According to one embodiment of the inventive process, the material obtained after step f) or step g) is deagglomerated, preferably in a pin-mill.

It is furthermore preferred according to the inventive process that the obtained material is heated to a temperature in the range from 60 to 150° C., preferably 70 to 130° C. and most preferably 80 to 110° C. to obtain a material with a total moisture content in the range from 0.05 to 0.2 wt.-%, preferably 0.01 to 0.1 wt.-% based on the total weight of the calcium carbonate-comprising material.

According to yet another embodiment of the inventive process, a) the partially dewatered calcium carbonate-comprising material is treated after dewatering step g) with at least one dispersing agent and re-diluted to obtain an aqueous suspension comprising a dispersed calcium carbonate-comprising material, and/or b) the partially dewatered calcium carbonate-comprising material and/or the dried calcium carbonate-comprising material is treated before or after dewatering or drying step g) with at least one saturated aliphatic linear or branched carboxylic acid and/or with at least one mono-substituted succinic anhydride and/or at least one mono-substituted succinic acid and/or salty reaction product(s) and/or with at least one phosphoric acid ester blend of one or more phosphoric acid mono-ester and/or reaction products thereof and one or more phosphoric acid di-ester and/or reaction products thereof to obtain a hydrophobized calcium carbonate-comprising material.

According to yet another embodiment of the inventive process, the at least one calcium carbonate-comprising material obtained in step f) has a) a BET specific surface area of ≤15.0 m$^2$/g, preferably in the range from 1.0 to 15.0 m$^2$/g, more preferably from 2.0 to 14.0 m$^2$/g, and most preferably from 2.5 to 13.0 m$^2$/g, and/or b) a lower ratio of particles having an average particle size $d_{80}$ value to particles having an average particle size $d_{20}$ value [$d_{80}/d_{20}$] than a calcium carbonate-comprising material that is obtained in an identical manner but without pre-heating step b) and contacting step d) and/or storing step f).

It is furthermore preferred according to the inventive process that the at least one calcium carbonate-comprising material obtained in step g) has a) a BET specific surface area of ≤15.0 m$^2$/g, preferably in the range from 1.0 to 15.0 m$^2$/g, more preferably from 2.0 to 14.0 m$^2$/g, and most preferably from 2.5 to 13.0 m$^2$/g, and/or b) a lower ratio of particles having an average particle size $d_{80}$ value to particles having an average particle size $d_{20}$ value [$d_{80}/d_{20}$] than a calcium carbonate-comprising material that is obtained in an identical manner but without pre-heating step b) and contacting step d) and/or storing step f).

The inventive use of carbonate-comprising material obtainable by the inventive process as described in the above first aspect includes the use in paper and board applications, in cosmetics, in caulks and sealants, in adhesives, in paints and coatings, preferably in underbody coatings or in plastic applications, fibres and non-wovens, for fibre applications and for the replacement of precipitated calcium carbonate, and also in plastics applications are selected from the group consisting of film applications, preferably blown film applications breathable film applications, biaxially oriented films, preferably polyethyleneterephthalate-, polyamide-, polyethylene- or polypropylene-comprising biaxially oriented films; granulates; pipes; technical profiles; wall panels; ceiling panels cladding panels; wire or cable insulations; sheets; fibres; flexible packaging for industrial and consumer applications, preferably roll stocks, bags, pouches, labels, wraps, liddings, shrink sleeves and stretch films; rigid packaging for industrial and consumer applications preferably plastic bottles, cups and containers; building and construction materials, preferably pipes and conduits, cladding and profiles, insulations, seals and gaskets; geotextiles; agriculture and horticulture materials preferably greenhouse materials, mulch films, tunnel, silage, bale wraps, boxes and crates; transportation and automotive applications preferably interior parts such as instrument and door panels, consoles, pillars and seating, exterior parts such as bumper fascia, fenders, tailgates, under the hood applications preferably air ducts, air intake manifolds, radiators and cooling hoses; electrical and electronic applications preferably CD players, DVD systems, personal computers and TV sets, notebooks, tablets, smartphones, cookers, refrigerators and freezers, washing machines, dishwashers, tools and office equipment; medical and health applications preferably disposable caps, gowns, masks, scrub suits and shoe covers, drapes, wraps and packs, sponges, dressings and wipes, bed linen, contamination control gowns, examination gowns, lab coats, isolation gowns, diagnostic medical machinery and medical devices; personal care products preferably absorbent hygiene products, baby diapers, feminine hygiene products and adult incontinence products, wipes, skin care products, depilatory strips; household and furniture products, preferably wood composites, decorative foils, floor coverings, flooring, kitchen ware, cleaners, pet care, lawn and garden articles; toys, sports and leisure articles preferably playhouses, building kits, play vehicles, sports and fitness devices, shoes, clothing and sportswear, safety equipment like helmets and kneepads, sports equipment and suit cases. The plastic may be PVC for window profiles, pipes, technical profiles such as cable- or wire conducts, wall-, ceiling-, or cladding panels or wire insulations.

Unless specified otherwise, the term "drying" refers to a process according to which at least a portion of water is removed from a material to be dried. Moreover, a "dried" material may be further defined by its total moisture content which, unless specified otherwise, is less than 3.0 wt.-%, preferably in the range from 0.05 to 0.2 wt.-%, more preferably in the range from 0.01 to 0.1 wt.-% based on the total weight of the calcium carbonate-comprising material. Unless indicated otherwise, the "total moisture content" of a material can be measured according to the Karl Fischer coulometric titration method, desorbing the moisture in an oven at 220° C. for 10 min and passing it continuously into a Karl Fischer coulometer (Mettler-Toledo coulometric KF Titrator C30, oven DO 0337) using dry nitrogen at 100 ml/min for 10 min. In this context, a calibration curve using water should be recorded and a blank of 10 min nitrogen flow without a sample has to be taken into account.

According to one embodiment of the present invention, the at least one calcium carbonate-comprising material obtained in step f) and optional step g) has a) a BET specific surface area of ≤15.0 m$^2$/g, preferably in the range from 1.0 to 15.0 m$^2$/g, more preferably from 2.0 to 14.0 m$^2$/g, and even more preferably from 2.5 to 13.0 m$^2$/g and most preferably from 2.5 to 4 m$^2$/g, and/or c) a lower ratio of particles having an average particle size $d_{80}$ value to particles having an average particle size $d_{20}$ value [$d_{80}/d_{20}$] than a calcium carbonate-containing material that is obtained by wet-grinding the same suspension of step a) to similar particle size but without pre-heating step b) and/or contacting step d) and/or storing step f).

As set out above, the inventive process for the preparation of an aqueous suspension comprising at least one calcium carbonate-containing material comprises the steps a), b), c) d), e) and f). In the following, it is referred to further details of the present invention and especially the foregoing steps of the inventive process for the preparation of an aqueous suspension comprising at least one calcium carbonate-comprising material. Those skilled in the art will understand that the embodiments described herein can be combined or applied together.

Characterization of Step a): Provision of at Least One Calcium Carbonate-Comprising Material According to step a) of the process of the present invention, a substantially dispersant-free aqueous suspension of at least one calcium carbonate-comprising material is provided.

The term "at least one" calcium carbonate-comprising material in the meaning of the present invention means that the calcium carbonate-comprising material comprises, preferably consists of, one or more kinds of calcium carbonate-comprising materials.

In one embodiment of the present invention, the at least one calcium carbonate-comprising material comprises, preferably consists of, one kind of calcium carbonate-comprising material. Alternatively, the at least one calcium carbonate-comprising material comprises, preferably consists of, two or more kinds of calcium carbonate-comprising materials. For example, the at least one calcium carbonate-comprising material comprises, preferably consists of, two or three kinds of calcium carbonate-comprising materials.

Preferably, the at least one calcium carbonate-comprising material is one kind of a calcium carbonate-comprising material.

It is appreciated that the at least one calcium carbonate-comprising material provided in step a) of the instant process can be any calcium carbonate-comprising material that is suitable for the envisaged purpose, i.e. use in paper and board applications, in cosmetics, in caulks and sealants, in adhesives, in paints and coatings, in fibre applications, in plastics applications or for the replacement of PCC in general.

The at least one calcium carbonate-comprising material according to the present invention is preferably a material that comprises at least 40.0 wt.-%, more preferably at least 60.0 wt.-%, even more preferably at least 80.0 wt.-%, and most preferably at least 90.0 wt.-%, such as at least 95.0 wt.-% or 98.0 wt.-%, of calcium carbonate, based on the total dry weight of the at least one calcium carbonate-comprising material.

The at least one calcium carbonate-comprising material is preferably dolomite and/or ground (or natural) calcium carbonate (NGCC). For example, the at least one calcium carbonate-comprising material is preferably dolomite or ground (or natural) calcium carbonate (NGCC). In one embodiment of the present invention, the at least one calcium carbonate-comprising material is ground (or natural) calcium carbonate (NGCC).

NGCC is understood to be a naturally occurring form of calcium carbonate, mined from sedimentary rocks such as limestone or chalk, or from metamorphic marble rocks and processed through a treatment such as grinding, screening and/or fractionizing in wet and/or dry form, for example by a cyclone or classifier.

In one embodiment of the present invention, the at least one calcium carbonate-comprising material is a NGCC, such as one or more of marble, limestone and/or chalk. Preferably, the at least one calcium carbonate-comprising material is marble or limestone. More preferably, the at least one calcium carbonate-comprising material is marble.

In a preferred embodiment the at least one calcium carbonate-comprising material is essentially free from PCC, i.e. contains less than 2 wt.-% of PCC, based on the calcium carbonate-comprising material and is more preferably free from PCC.

The at least one calcium carbonate-comprising material used as starting material in step a) is preferably in the form of a particulate material, and may have a particle size distribution as conventionally employed for the material(s) involved in the type of product to be used. In general, it is preferred that the at least one calcium carbonate-comprising material has a weight median particle size diameter $d_{50}$ in the range from 0.5 µm to 50.0 µm. For example, the at least one calcium carbonate-comprising material has a weight median particle size diameter $d_{50}$ in the range from 0.7 µm to 45.0 µm, more preferably from 1.0 µm to 40.0 µm and most preferably from 5 µm to 35 µm.

According to the inventive process, also relatively coarse starting materials can be used. In step a) calcium carbonate-comprising material having a content of particles with a particle diameter <1 µm of between 30 to 90 wt.-%, preferably between 35 and 65 wt.-% and most preferably between 40 and 60 wt.-%, based on the weight of the at least one calcium carbonate-comprising material can be used.

As used herein and as generally defined in the art, the "$d_{50}$" value is determined based on measurements made by using a Sedigraph™ III Plus of Micromeritics Instrument Corporation (operating instrument software version 1.04) and is defined as the size at which 50% (the median point) of the sample mass is accounted for by particles having a diameter finer than or equal to the specified value. The method and the instrument are known to the skilled person and are commonly used to determine grain size of fillers and pigments.

Additionally or alternatively, the at least one calcium carbonate-comprising material used as starting material in step a) has a $d_{95}$ value of ≤250.0 µm. For example, the at least one calcium carbonate-comprising material has a $d_{95}$ value of from 30.0 to 250.0 µm, preferably from 40.0 to 180.0 µm and most preferably from 50.0 to 150.0 µm.

In one embodiment of the present invention, the at least one calcium carbonate-comprising material used as starting material in step a) is a dry ground material, a material being wet ground and dried or a mixture of the foregoing materials, wet ground materials are preferred.

In one embodiment of the present invention, the at least one calcium carbonate-comprising material is a material being wet ground and optionally dried and re-diluted with water in order to form an aqueous suspension comprising the wet-ground calcium carbonate-comprising material. Alternatively, the at least one calcium carbonate-comprising material is a material being dry ground and re-diluted with water in order to form an aqueous suspension comprising the dry ground calcium carbonate-comprising material. Wet-grinding and dry-grinding of the at least one calcium carbonate-comprising material can be carried out by any conventional grinding means known to the skilled person. For example, the wet-grinding of the at least one calcium carbonate-comprising material can be carried out in a vertical agitated bead mill. Furthermore, the drying can be carried out by any conventional drying or heating means known to the skilled person.

It is appreciated that the at least one calcium carbonate-comprising material is provided in form of an aqueous suspension. For example, the aqueous suspension comprises, preferably consists of, the at least one calcium carbonate-comprising material and water. Alternatively, the aqueous suspension comprises, preferably consists of, the at least one calcium carbonate-comprising material, water and an organic solvent. If the aqueous suspension comprises an organic solvent, the aqueous suspension comprises the organic solvent in an amount of from 0.1 to 20.0 wt.-%, preferably from 0.5 to 15.0 wt.-% and most preferably from 1.0 to 10.0 wt.-%, based on the total weight of the aqueous suspension.

In one embodiment of the present invention, the aqueous suspension has solids content, i.e. the at least one calcium carbonate-comprising material, of from 5.0 wt.-% to 60.0 wt.-%, preferably from 10.0 wt.-% to 55.0 wt.-% and most preferably from 15.0 wt.-% to 50.0 wt.-%, based on the total weight of the aqueous suspension.

The water to be used in the aqueous suspension may be any water available such as process water, such as process water coming from water treatment systems and/or tap water and/or deionised water. Preferably, the water used for preparing the aqueous suspension of step a) is process water.

It is one requirement of the present invention that the aqueous suspension is substantially free of dispersants.

The expression "substantially dispersant-free" refers to systems in which the amount of a dispersant, such as sodium polyacrylate and/or sodium hydrogen phosphate, is too low to hinder the preparation of the inventive at least one calcium carbonate-comprising material. Preferably, the aqueous suspension provided in step a) comprises dispersants in an amount of <0.05 wt.-%, more preferably <0.02 wt.-% and most preferably <0.01 wt.-%, based on the total dry weight of the at least one calcium carbonate-comprising material. In other words, the term "substantially dispersant-free" means that the aqueous suspension contains no dispersant or a sub-effective amount of dispersant. A "sub-effective amount of dispersant" in the meaning of the present invention corresponds to an amount of dispersant which does not cause any measurable influence or change of the viscosity of the moist calcium carbonate containing material, i.e. the slurry containing the calcium carbonate solids. In other words, the viscosity of the moist calcium carbonate containing material containing a sub-effective amount of dispersant is substantially the same as in the complete absence of a dispersant. A sub-effective amount of dispersant typically is less than about 0.05 wt.-%, based on the dry calcium carbonate containing material, for example, less than about 0.02 wt.-%, less than about 0.01 wt.-%, based on the dry calcium carbonate containing material. A "dispersant" in the meaning of the present invention is, for example, a sodium poly(meta)acrylate, sodium polyphosphate and derivates and blends of the foregoing. In one embodiment of the present invention, the aqueous suspension of step a) is free of dispersants, i.e. the aqueous suspension comprises no dispersants.

It is appreciated that such dispersants interfere with the present process such that a calcium carbonate-comprising material in the meaning of the present invention, i.e. a calcium carbonate-comprising material having a ratio of particles having an average particle size $d_{80}$ value to particles having an average particle size $d_{20}$ value $[d_{80}/d_{20}]$ in the range from 1.5 to 4, is not obtained.

Accordingly, it is preferred that no dispersant is added before and/or during process step a) and/or step b) and/or step c) and/or step d), and/or step e) and/or step f). More preferably, no dispersant is added before and during process step a) and step b) and step c) and step d) and step e) and step f).

Characterization of Step b): Pre-Heating the Aqueous Suspension

According to step b) of the process of the present invention, the suspension of step a) is pre-heated to a temperature of from 40 to 95° C. at ambient pressure.

In one embodiment of the present invention, the aqueous suspension is adjusted to a temperature of from 50 to 95° C., preferably from 60 to 90° C., more preferably from 75 to 85° C.

The pre-heating in the instant process can be carried out by any conventional heating means known to the skilled person.

The temperature in the aqueous suspension varies due to variation in water temperature or quality of water and, thus, the temperature of the aqueous suspension may be adjusted frequently. Preferably, the temperature is controlled continuously. Alternatively, the temperature is controlled repeatedly.

Pre-heating of the aqueous suspension of step a) can be carried out by any conventional heating means known to the skilled person. For example, the pre-heating of the aqueous suspension of step a) can be carried out by using a heat exchanging device.

In a preferred embodiment the solid content of the slurry is adjusted to 20 to 30%, more preferably 25% before the preheating step b).

In one embodiment preheating step b) is carried out under increased pressure.

It is appreciated that the expression "before pre-heating step b)" refers to the time period in which the aqueous suspension of step a) has room temperature or an elevated temperature already obtained from previous processing steps at ambient pressure and the heating up of the suspension to the desired pre-heating temperature has not yet started. The expression "during pre-heating step b)" refers to the time period in which the aqueous suspension of step a) is heated up to the pre-heating temperature of from 40 to 95° C. at ambient pressure. The expression "after pre-heating step b)" refers to the time period after which the aqueous suspension has reached the pre-heating temperature of from 40 to 95° C. at ambient pressure. The expression "before wet-grinding step c)" refers to the time period before which the wet-grinding of step c) has started. The expression "during wet-grinding step c)" refers to the time period in which the aqueous suspension of step b) is wet-ground. The expression "after wet-grinding step c)" refers to the time period after which the wet-grinding of the aqueous suspension of step c) has been stopped. The terms "after", "during" and "before" are used analogous for process steps d), e), f) and optional step g).

Characterization of Step c): Wet-Grinding the Pre-Heated Aqueous Suspension

According to step c) of the process of the present invention, the pre-heated suspension of step b) is wet-ground in at least one grinding step for obtaining an aqueous suspension of at least one wet ground calcium carbonate-comprising material, preferably having a ratio of particles having an average particle size $d_{80}$ value to particles having an average particle size $d_{20}$ value $[d_{80}/d_{20}]$ in the range from 3 to 8, preferably in the range from 3.5 to 7 and most preferably in the range from 4 to 6.

In general, wet-grinding step c) can be carried out with any conventional grinding device known to the skilled man. For example, wet-grinding step c) can be performed by using a bead or media mill, such as a vertical or horizontal bead mill or vertical or horizontal media mill, and/or other such processes known to the skilled man.

In one embodiment of the present invention, the grinding device, such as a vertical bead mill, comprises grinding media. For example, the grinding device is filled with grinding media in an amount of at least 10.0 vol.-%, preferably at least 50.0 vol.-%, more preferably from 50.0 to 80.0 vol.-% and most preferably from 60.0 to 80.0 vol.-%, such as about 70.0 vol.-%, based on the total volume of the grinding device.

The wet-grinding can be performed by using a great variety of grinding media. For example, the grinding media can be made up of ceramic media, zirconia ($ZrO_2$), ceria-stabilized high dense grinding media, glass or mixtures thereof. In one embodiment of the present invention, the grinding media is made up of ceramic media or ceria-stabilized high dense grinding media with a specific gravity of greater or equal than about 5 g/cm$^3$.

Additionally or alternatively, the grinding media may have a specific diameter. For example, the grinding media have a weight median particle size diameter $d_{50}$ of 0.1 to 2.5 mm, preferably of 0.2 to 2.0 mm and most preferably of 0.3 to 1.6 mm.

Additionally or alternatively, the grinding media may have a specific density. For example, the grinding media may have a density of 3.0 to 10.0 g/cm$^3$, preferably of 4.0 to 8.0 g/cm$^3$ and most preferably of 5.0 to 7.0 g/cm$^3$.

It is appreciated that wet-grinding step c) is preferably carried out until the at least one calcium carbonate-comprising material has the desired fineness.

For example, wet-grinding step c) is carried out until at least 20.0 wt.-%, preferably at least 25.0 wt.-% of the at least one calcium carbonate-comprising material has a weight median particle size diameter of ≤1.0 μm. In one embodiment of the present invention, wet-grinding step c) is carried out until at least 30.0 wt.-%, preferably at least 35.0 wt.-%, more preferably at least 40.0 wt.-% and most preferably at least 45.0 wt.-% of the at least one calcium carbonate-comprising material has a weight median particle size diameter of ≤1.0 μm.

The starting temperature of wet-grinding step c), i.e. of the aqueous suspension, preferably corresponds to the temperature of the pre-heated suspension obtained in step b). Accordingly, it is appreciated that wet-grinding step c) is preferably carried out at a starting temperature of from 40 to 95° C., preferably from 60 to 80° C., more preferably from 75 to 85° C.

The temperature can preferably be controlled and maintained at said starting temperature while step c) is carried out. In this respect, it is to be noted that the term "the temperature is maintained" during said process step in the meaning of the present invention relates to a temperature which does preferably not exceed the starting temperature by more than 5° C.; i.e. if the starting temperature is for example adjusted to a temperature of 40° C., the temperature during process step c) may not exceed 45° C.

Alternatively, the starting temperature of process step c) is allowed to rise while wet-grinding step c) is carried out. However, due to the dissipation-/friction heat generated during wet-grinding the temperature of the mixture may rise to temperatures of 90° C. and more. The maximum temperature at the mill outlet in this embodiment of the process is preferably about the boiling point of water and most preferably the maximum temperature reached during step c) is about 100° C. at ambient pressure. For example, the maximum temperature reached during process step c) is preferably between 80 and 99° C.

The aqueous suspension comprising at least one calcium carbonate-comprising material obtained in wet-grinding step c) preferably has solids content of from 5.0 wt.-% to 60.0 wt.-%, preferably from 10.0 wt.-% to 55.0 wt.-%, more preferably from 15.0 wt.-% to 50.0 wt.-% and most preferably from 20.0 wt.-% to 45.0 wt.-%, based on the total weight of the aqueous suspension.

In the case where the obtained aqueous suspension has a solid contents of the at least one calcium carbonate-comprising material above or below the desired range the aqueous suspension may be diluted with water or up-concentrated by any conventional process known to the skilled person to obtain a suspension of said desired solid content.

In one embodiment of the present invention, the aqueous suspension comprising at least one calcium carbonate-comprising material obtained in wet-grinding step c) preferably has a pH measured at 25° C. of ≥9.0, preferably from 10.0 to 13.0 and most preferably from 11.0 to 12.5.

The time which may be required for carrying out the instant process step is the time required to almost complete the transformation of the at least one calcium carbonate-comprising material into the at least one calcium carbonate-comprising material featuring the desired characteristics. Such almost complete transformation of the at least one calcium carbonate-comprising material is preferably obtained within 2 hours, more preferably within 1 hour, still more preferably within 45 minutes, even more preferably within 30 minutes and most preferably within 20 minutes, calculated from the start of wet-grinding the pre-heated aqueous suspension comprising the at least one calcium carbonate-comprising material optionally in the presence of at least one base.

Characterization of Step d): Contacting the Aqueous Suspension with at Least One Base According to step d) of the process of the present invention, the aqueous suspension of step a) is contacted before and/or during and/or after wet-grinding step c) and/or before and/or during and/or after removal step e) with at least one base for obtaining an aqueous suspension having a pH measured at 25° C. of ≥9.0. It is preferred that the contacting step d) is carried out after wet-grinding step c) and more preferred after removal step e).

The expression "at least one base" in the meaning of the present invention means that the base comprises, preferably consists of, one or more kinds of bases.

In one embodiment of the present invention, the at least one base comprises, preferably consists of, one kind of base. Alternatively, the at least one base comprises, preferably consists of, two or more kinds of bases. For example, the at least one base comprises, preferably consists of, two or three kinds of bases.

In one embodiment of the present invention, the at least one base is one kind of base.

It is appreciated that the at least one base of step d) of the instant process can be any base that is suitable for adjusting the pH of the aqueous suspension to a pH measured at 25° C. of ≥9.0.

In one embodiment of the present invention, the aqueous suspension is contacted with the at least one base such that the obtained aqueous suspension has a pH measured at 25° C. of from 10.0 to 13.0 and preferably from 11.0 to 12.5.

In one embodiment of the present invention, the at least one base is added in contacting step d) in an amount of ≥0.05 wt.-%, preferably of ≥0.1 wt.-%, more preferably of ≥0.2 wt.-% and most preferably of from 0.2 to 1.0 wt.-%, based on the total dry weight of the calcium carbonate-comprising material.

For the sake of completeness, it is to be noted that the amount of the at least one base is calculated as active material on dry matter calcium carbonate-comprising material.

Additionally or alternatively, it is preferred that the at least one base of contacting step d) is at least one alkali metal hydroxide and/or at least one earth alkali metal hydroxide.

If the at least one base is at least one alkali metal hydroxide, the at least one alkali metal hydroxide is selected from the group comprising lithium hydroxide, sodium hydroxide, potassium hydroxide and mixtures thereof. In one embodiment of the present invention, the at least one alkali metal hydroxide is preferably selected from sodium hydroxide and/or potassium hydroxide. For example, the at least one alkali metal hydroxide is sodium hydroxide or potassium hydroxide. It is preferred that the at least one alkali metal hydroxide is sodium hydroxide.

If the at least one base is at least one earth alkali metal hydroxide, the at least one earth alkali metal hydroxide is selected from the group comprising magnesium hydroxide, calcium hydroxide and mixtures thereof. For example, the at least one earth alkali metal hydroxide is magnesium hydroxide or calcium hydroxide. It is preferred that the at least one earth alkali metal hydroxide is calcium hydroxide.

In one embodiment of the present invention, the at least one base of contacting step d) is sodium hydroxide.

Another preferred base for step d) according to the present invention is sodium carbonate.

The at least one base can be provided in step d) in an aqueous environment or as a dry material. In one embodiment of the present invention, the at least one base is provided in step d) in an aqueous environment. For example, the at least one base is provided in step d) in an aqueous environment comprising, preferably consisting of, water.

The expression "aqueous environment" refers to a system comprising, preferably consisting of, water. For example, the aqueous environment consists of water. If the aqueous environment consists of water, the water to be used can be any water available such as process water, such as process water coming from water treatment systems, and/or tap water and/or deionised water. The aqueous environment is preferably free of dispersants and suspended solid materials. In one embodiment of the present invention, the aqueous environment is preferably free of materials being reactive towards calcium carbonate-comprising materials.

If the at least one base is added to the aqueous suspension in an aqueous environment, the aqueous environment comprising, preferably consisting of, the at least one base has preferably an elevated temperature as an aqueous environment having room temperature may inversely affect the time required for pre-heating the aqueous suspension. Therefore, the temperature of the aqueous environment comprising, preferably consisting of, the at least one base used in contacting step d) should preferably be above room temperature but equal to or below the temperature used in pre-heating step b). Alternatively, the temperature of the aqueous environment comprising, preferably consisting of, the at least one base used in contacting step d) is of about room temperature, i.e. such as from 20 to 24° C.

Preferably, the aqueous suspension is contacted with the at least one base being a dry material.

In one embodiment of the present invention, the aqueous suspension of step a) is contacted with the at least one base in one or several portions. If the at least one base is added in several portions, the aqueous suspension of step a) is contacted with the at least one base preferably in two to five portions, more preferably in two to four portions, even more preferably in two to three portions and most preferably in two portions.

It is appreciated that the aqueous suspension of step a) is contacted with the at least one base preferably in one portion.

Characterization of Step e): Removal of Coarse Particles (Diameter >20 Um)

The removal of coarse particles can be carried out by all means known to the person skilled in the art. Preferably for the removal of coarse particles a centrifuge and/or a disc separator are used.

The expression "coarse particles" in the gist of the present invention refers to particles with a diameter >20 µm. Coarse particles are inter alia calcium carbonate-comprising material, contaminants, mica, quartz or parts of the grinding media.

In a preferred embodiment >90 wt.-% of particles with a diameter >100 µm and >70 wt.-% of particles with a diameter >20 µm and more preferably essentially all particles with a diameter >100 µm and >90 wt.-% of particles with a diameter >20 µm are removed.

In another embodiment the BET specific surface are of ≤15.0 m$^2$/g, preferably in the range from 1.0 to 15.0 m$^2$/g, more preferably from 2.0 to 14.0 m$^2$/g, and most preferably from 3.0 to 13.0 m$^2$/g after step e).

Characterization of Step f): Storing the Aqueous Suspension

The process according to present invention comprises process step f) of storing the aqueous suspension obtained in removal step e).

It is appreciated that the aqueous suspension comprising at least one calcium carbonate-comprising material obtained in removal step e) according to one preferred embodiment can be directly used, i.e. without further process steps between step e) and f), for storing. Accordingly, the aqueous suspension stored in step f) may have a solids content of from 5.0 wt.-% to 60.0 wt.-%, preferably from 10.0 wt.-% to 55.0 wt.-%, more preferably from 15.0 wt.-% to 50.0 wt.-% and most preferably from 20.0 wt.-% to 50.0 wt.-%, based on the total weight of the aqueous suspension.

The instant process comprises storing step f), which is carried out at elevated temperature. The aqueous suspension obtained in removal step e) is stored in step f) at a temperature of from 70 to 140° C., preferably from 75 to 130° C. and most preferably from 80 to 95° C.

Furthermore, the storing is carried out for a sufficiently long period of time allowing a complete or almost complete transformation of the at least one calcium carbonate-comprising material to the desired crystal morphology. During storing step f), the aqueous suspension obtained in step e) is stored for a period of time of 0.25 to 8 hours, for obtaining an aqueous suspension of at least one calcium carbonate-comprising material having a ratio of particles having an average particle size $d_{80}$ value to particles having an average particle size $d_{20}$ value [$d_{80}/d_{20}$] in the range from 1.5 to 4.0. Preferably, the aqueous suspension is stored at a temperature of from 75 to 130° C. and most preferably from 80 to 95° C., and/or for a period of time of 0.1 to 7 hours, preferably 0.5 to 3.5 hours, more preferably 0.75 to 2.5 hours and most preferably 1 to 2 hours.

The storing step can be conducted under increased pressure.

In one embodiment the slurry is cooled to 20 to 60° C. preferably 30 to 50 most preferably 40° C. after the storing step f).

For obtaining a weakly alkaline aqueous suspension comprising at least one calcium carbonate-comprising material, the aqueous suspension may be after storing step f), treated with at least one acid such as to obtain an aqueous suspension comprising at least one calcium carbonate-comprising material having a pH measured at 25° C. of ≤10.5, preferably from 8.0 to 10.5 and most preferably from 8.5 to 10.0.

The expression "at least one" acid in the meaning of the present invention means that the acid comprises, preferably consists of, one or more kinds of acids.

In one embodiment of the present invention, the at least one acid comprises, preferably consists of, one kind of acid. Alternatively, the at least one acid comprises, preferably consists of, two or more kinds of acids. For example, the at least one acid comprises, preferably consists of, two or three kinds of acids.

In one embodiment of the present invention, the at least one acid is one kind of acid.

The term "acid" in the meaning of the present invention refers to an acid in accordance with the Brønsted-Lowry concept.

It is appreciated that the at least one acid that may be added to the aqueous suspension of the instant process can be any acid that is suitable for adjusting the pH of the aqueous suspension to a pH measured at 25° C. of ≤10.0.

For example, the at least one acid is selected from the group comprising phosphoric acid, citric acid, carbonic acid, hydrochloric acid, dispersing agent, such as sodium and/or potassium and/or ammonium salts of at least partly neutralized homopolymers or copolymers of acrylic acid or maleic acid, and mixtures thereof.

If the at least one acid is a dispersing agent, the aqueous suspension obtained from the instant process is preferably dewatered and then re-diluted with water in the presence of the dispersing agent. Dispersing agents are well known to the skilled person and are available from a great variety of sources.

In one embodiment of the present invention, the aqueous suspension comprising at least one calcium carbonate-comprising material is free of chelating agents and/or conjugated bases.

Characterization of Step g): Dewatering and Optionally Drying

Optionally, the aqueous suspension comprising at least one calcium carbonate-comprising material obtained in storing step f) can be dewatered and optionally dried in process step g), optionally up to the point of obtaining a partially dewatered calcium carbonate-comprising material or a dried calcium carbonate-comprising material.

The dewatering can be carried out by any means known to the skilled man, preferred is the use of a decanter and/or a centrifuge. In one embodiment the calcium carbonate-comprising material is re-diluted, preferably with pure water and dewatered again to wash out residual base. This procedure can be repeated, preferably twice. When sodium carbonate is used as base it is preferred to repeat the re-dilution dewatering procedure once, this means carrying out both steps two times. In one embodiment the residual base is removed by using a washing filter, preferably by displacement washing i.e. in one step. The use of e.g. belt filters or drum filters with washing zone allows to carry out the dewatering/washing sequence directly in one machine.

In one embodiment the calcium carbonate-comprising material is dewatered and the residual base is washed out in one step on a feasible process equipment, e.g. wash filters, vacuum drum filters, press filters, press filters with washing, known to the skilled person. The inventors of the present invention surprisingly found that washing out residual base yields a calcium carbonate-comprising material with a lower moisture pick-up susceptibility than a calcium carbonate-comprising material manufactured without washing out residual base. A reduction of the water pick-up by a factor of 20 may be achieved by applying a step of washing out residual base.

For drying the calcium carbonate-comprising material thermal methods like flash- or spray-drying are preferred.

The expression "dried" as used herein is understood to refer to a calcium carbonate-containing material having a total moisture content of less than 3.0 wt.-%, preferably less than 2.0 wt.-%, more preferably less than 1.5 wt.-% and most preferably of less than 1.0 wt.-%, based on the total weight of the calcium carbonate-comprising material. In one embodiment of the present invention, the calcium carbonate-comprising material has a total moisture content of less than 0.8 wt.-%, preferably less than 0.7 wt.-% and most preferably of less than 0.6 wt.-%, based on the total weight of the calcium carbonate-comprising material. For example, the calcium carbonate-comprising material has a total moisture content of 0.05 to 0.2 wt.-%, preferably 0.01 to 0.1 wt.-% based on the total weight of the calcium carbonate-comprising material.

If the aqueous suspension described above is partially dewatered, the partially dewatered calcium carbonate-comprising material obtained in step g) is preferably in form of an aqueous suspension having high solids content, i.e. the solids content is above the solids content of the aqueous suspension obtained after storing step f) of the instant process. For example, the partially dewatered calcium carbonate-comprising material obtained in step g) is in form of an aqueous suspension having solids content from 20.0 to 70.0 wt.-%, preferably from 25.0 to 65.0 wt.-%, and most preferably from 30.0 to 60.0 wt.-%, based on the total weight of the aqueous suspension.

If the aqueous suspension described above is dried, the solids (i.e. dry or containing as little water that it is not in a fluid form) of calcium carbonate-comprising material obtained in step g) can be in the form of granules or a powder.

In another embodiment the calcium carbonate-comprising material is deagglomerated. This step is preferably carried out in a pin-mill.

According to one embodiment of the present invention the calcium carbonate-comprising material obtained after the drying or deagglomeration step is heated to a temperature in the range from 60 to 150° C., preferably 70 to 130° C. and most preferably 80 to 110° C. to obtain a material with a moisture content in the range from 0.05 to 0.2 wt.-%, preferably 0.01 to 0.1 wt.-%.

In the case of a dried product and/or a partially dewatered calcium carbonate-comprising material, the product and/or material can additionally be treated with an aliphatic linear or branched carboxylic acid or at least one mono-substituted succinic anhydride and/or at least one mono-substituted succinic acid and/or salty reaction product(s) thereof. For example, the dried calcium carbonate-comprising material and/or partially dewatered calcium carbonate-comprising material can be treated with an aliphatic linear or branched carboxylic acid having between 5 and 24 carbon atoms during and/or before and/or after drying. Preferably, the dried calcium carbonate-comprising material and/or partially dewatered calcium carbonate-comprising material is treated with an aliphatic linear or branched carboxylic acid having between 5 and 24 carbon atoms before or after drying. More preferably, the dried calcium carbonate-comprising material and/or partially dewatered calcium carbonate-comprising material is treated with an aliphatic linear or branched carboxylic acid having between 5 and 24 carbon atoms before drying.

The aliphatic linear or branched carboxylic acid in the meaning of the present invention may be selected from one or more straight chain, branched chain, saturated, unsaturated and/or alicyclic carboxylic acids. Preferably, the aliphatic linear or branched carboxylic acid is a monocarboxylic acid, i.e. the aliphatic linear or branched carboxylic acid is characterized in that a single carboxyl group is present. Said carboxyl group is placed at the end of the carbon skeleton.

In one embodiment of the present invention, the aliphatic linear or branched carboxylic acid is selected from saturated unbranched carboxylic acids, that is to say the aliphatic linear or branched carboxylic acid is preferably selected from the group of carboxylic acids consisting of pentanoic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, heneicosylic acid, behenic acid, tricosylic acid, lignoceric acid and mixtures thereof.

In another embodiment of the present invention, the aliphatic linear or branched carboxylic acid is selected from the group consisting of octanoic acid, decanoic acid, lauric acid, myristic acid, palmitic acid, stearic acid, arachidic acid and mixtures thereof. Preferably, the aliphatic linear or branched carboxylic acid is selected from the group consisting of myristic acid, palmitic acid, stearic acid and mixtures thereof.

For example, the aliphatic linear or branched carboxylic acid is stearic acid.

In another embodiment the dried calcium carbonate-comprising material and/or partially dewatered calcium carbonate-comprising material can be treated with at least one phosphoric acid ester blend of one or more phosphoric acid mono-ester and/or reaction products thereof and one or more phosphoric acid di-ester and/or reaction products thereof.

The term "reaction products" of the phosphoric acid mono-ester and one or more phosphoric acid di-ester in the meaning of the present invention refers to products obtained by contacting the calcium carbonate with the at least one phosphoric acid ester blend. Said reaction products are formed between at least a part of the applied phosphoric acid ester blend and reactive molecules located at the surface of the calcium carbonate particles.

The term "phosphoric acid mono-ester" in the meaning of the present invention refers to an o-phosphoric acid molecule mono-esterified with one alcohol molecule selected from unsaturated or saturated, branched or linear, aliphatic or aromatic alcohols having a total amount of carbon atoms from $C_6$ to $C_{30}$, preferably from $C_8$ to $C_{22}$, more preferably from $C_8$ to $C_{20}$ and most preferably from $C_8$ to $C_{18}$ in the alcohol substituent.

The term "phosphoric acid di-ester" in the meaning of the present invention refers to an o-phosphoric acid molecule di-esterified with two alcohol molecules selected from the same or different, unsaturated or saturated, branched or linear, aliphatic or aromatic alcohols having a total amount of carbon atoms from $C_6$ to $C_{30}$, preferably from $C_8$ to $C_{22}$, more preferably from $C_8$ to $C_{20}$ and most preferably from $C_8$ to $C_{18}$ in the alcohol substituent.

It is appreciated that the expression "one or more" phosphoric acid mono-ester means that one or more kinds of phosphoric acid mono-ester may be present in the phosphoric acid ester blend.

Accordingly, it should be noted that the one or more phosphoric acid mono-ester may be one kind of phosphoric acid mono-ester. Alternatively, the one or more phosphoric acid mono-ester may be a mixture of two or more kinds of phosphoric acid mono-ester. For example, the one or more phosphoric acid mono-ester may be a mixture of two or three kinds of phosphoric acid mono-ester, like two kinds of phosphoric acid mono-ester.

In one embodiment of the present invention, the one or more phosphoric acid mono-ester consists of an o-phosphoric acid molecule esterified with one alcohol selected from unsaturated or saturated, branched or linear, aliphatic or aromatic alcohols having a total amount of carbon atoms from $C_6$ to $C_{30}$ in the alcohol substituent. For example, the one or more phosphoric acid mono-ester consists of an o-phosphoric acid molecule esterified with one alcohol selected from unsaturated or saturated, branched or linear, aliphatic or aromatic alcohols having a total amount of carbon atoms from $C_8$ to $C_{22}$, more preferably from $C_8$ to $C_{20}$ and most preferably from $C_8$ to $C_{18}$ in the alcohol substituent.

In one embodiment of the present invention, the one or more phosphoric acid mono-ester is selected from the group comprising hexyl phosphoric acid mono-ester, heptyl phosphoric acid mono-ester, octyl phosphoric acid mono-ester, 2-ethylhexyl phosphoric acid mono-ester, nonyl phosphoric acid mono-ester, decyl phosphoric acid mono-ester, undecyl phosphoric acid mono-ester, dodecyl phosphoric acid mono-ester, tetradecyl phosphoric acid mono-ester, hexadecyl phosphoric acid mono-ester, heptylnonyl phosphoric acid mono-ester, octadecyl phosphoric acid mono-ester, 2-octyl-1-decylphosphoric acid mono-ester, 2-octyl-1-dodecylphosphoric acid mono-ester and mixtures thereof.

For example, the one or more phosphoric acid mono-ester is selected from the group comprising 2-ethylhexyl phosphoric acid mono-ester, hexadecyl phosphoric acid mono-ester, heptylnonyl phosphoric acid mono-ester, octadecyl phosphoric acid mono-ester, 2-octyl-1-decyl phosphoric acid mono-ester, 2-octyl-1-dodecyl phosphoric acid mono-ester and mixtures thereof. In one embodiment of the present invention, the one or more phosphoric acid mono-ester is 2-octyl-1-dodecyl phosphoric acid mono-ester.

It is appreciated that the expression "one or more" phosphoric acid di-ester means that one or more kinds of phosphoric acid di-ester may be present in the coating layer of the calcium carbonate and/or the phosphoric acid ester blend.

Accordingly, it should be noted that the one or more phosphoric acid di-ester may be one kind of phosphoric acid di-ester. Alternatively, the one or more phosphoric acid di-ester may be a mixture of two or more kinds of phosphoric acid di-ester. For example, the one or more phosphoric acid di-ester may be a mixture of two or three kinds of phosphoric acid di-ester, like two kinds of phosphoric acid di-ester.

In one embodiment of the present invention, the one or more phosphoric acid di-ester consists of an o-phosphoric acid molecule esterified with two alcohols selected from unsaturated or saturated, branched or linear, aliphatic or aromatic alcohols having a total amount of carbon atoms from $C_6$ to $C_{30}$ in the alcohol substituent. For example, the one or more phosphoric acid di-ester consists of an o-phosphoric acid molecule esterified with two fatty alcohols selected from unsaturated or saturated, branched or linear, aliphatic or aromatic alcohols having a total amount of carbon atoms from $C_8$ to $C_{22}$, more preferably from $C_8$ to $C_{20}$ and most preferably from $C_8$ to $C_{18}$ in the alcohol substituent.

It is appreciated that the two alcohols used for esterifying the phosphoric acid may be independently selected from the same or different, unsaturated or saturated, branched or linear, aliphatic or aromatic alcohols having a total amount of carbon atoms from C6 to C30 in the alcohol substituent. In other words, the one or more phosphoric acid di-ester may comprise two substituents being derived from the same alcohols or the phosphoric acid di-ester molecule may comprise two substituents being derived from different alcohols.

In one embodiment of the present invention, the one or more phosphoric acid di-ester consists of an o-phosphoric acid molecule esterified with two alcohols selected from the same or different, saturated and linear and aliphatic alcohols having a total amount of carbon atoms from $C_6$ to $C_{30}$, preferably from $C_8$ to $C_{22}$, more preferably from $C_8$ to $C_{20}$ and most preferably from $C_8$ to $C_{18}$ in the alcohol substituent. Alternatively, the one or more phosphoric acid di-ester consists of an o-phosphoric acid molecule esterified with two alcohols selected from the same or different, saturated and branched and aliphatic alcohols having a total amount of carbon atoms from $C_6$ to $C_{30}$, preferably from $C_8$ to $C_{22}$, more preferably from $C_8$ to $C_{20}$ and most preferably from $C_8$ to $C_{18}$ in the alcohol substituent.

In one embodiment of the present invention, the one or more phosphoric acid di-ester is selected from the group comprising hexyl phosphoric acid di-ester, heptyl phosphoric acid di-ester, octyl phosphoric acid di-ester, 2-ethylhexyl phosphoric acid di-ester, nonyl phosphoric acid di-ester, decyl phosphoric acid di-ester, undecyl phosphoric acid di-ester, dodecyl phosphoric acid di-ester, tetradecyl phosphoric acid di-ester, hexadecyl phosphoric acid di-ester, heptylnonyl phosphoric acid di-ester, octadecyl phosphoric acid di-ester, 2-octyl-1-decyl phosphoric acid di-ester, 2-octyl-1-dodecyl phosphoric acid di-ester and mixtures thereof.

For example, the one or more phosphoric acid di-ester is selected from the group comprising 2-ethylhexyl phosphoric acid di-ester, hexadecyl phosphoric acid di-ester, heptylnonyl phosphoric acid di-ester, octadecyl phosphoric acid di-ester, 2-octyl-1-decyl phosphoric acid di-ester, 2-octyl-1-dodecyl phosphoric acid di-ester and mixtures thereof.

In one embodiment of the present invention, the one or more phosphoric acid di-ester is 2-octyl-1-dodecyl phosphoric acid di-ester.

In one embodiment of the present invention, the one or more phosphoric acid mono-ester is selected from the group comprising 2-ethylhexyl phosphoric acid mono-ester, hexadecyl phosphoric acid mono-ester, heptylnonyl phosphoric acid mono-ester, octadecyl phosphoric acid mono-ester, 2-octyl-1-decyl phosphoric acid mono-ester, 2-octyl-1-dodecyl phosphoric acid mono-ester and mixtures thereof and the one or more phosphoric acid di-ester is selected from the group comprising 2-ethylhexyl phosphoric acid di-ester, hexadecyl phosphoric acid di-ester, heptylnonyl phosphoric acid di-ester, octadecyl phosphoric acid di-ester, 2-octyl-1-decyl phosphoric acid di-ester, 2-octyl-1-dodecyl phosphoric acid di-ester and mixtures thereof.

For example, at least a part of the accessible surface area of the calcium carbonate comprises a phosphoric acid ester blend of one phosphoric acid mono-ester and/or reaction products thereof and one phosphoric acid di-ester and/or reaction products thereof. In this case, the one phosphoric acid mono-ester is selected from the group comprising 2-ethylhexyl phosphoric acid mono-ester, hexadecyl phosphoric acid mono-ester, heptylnonyl phosphoric acid mono-ester, octadecyl phosphoric acid mono-ester, 2-octyl-1-decyl phosphoric acid mono-ester and 2-octyl-1-dodecyl phosphoric acid mono-ester, the one phosphoric acid di-ester is selected from the group comprising 2-ethylhexyl phosphoric acid di-ester, hexadecyl phosphoric acid di-ester, heptylnonyl phosphoric acid di-ester, octadecyl phosphoric acid di-ester, 2-octyl-1-decyl phosphoric acid di-ester and 2-octyl-1-dodecyl phosphoric acid di-ester.

The phosphoric acid ester blend comprises the one or more phosphoric acid mono-ester and/or reaction products thereof to the one or more phosphoric acid di-ester and/or reaction products thereof in a specific molar ratio. In particular, the molar ratio of the one or more phosphoric acid mono-ester and/or reaction products thereof to the one or more phosphoric acid di-ester and/or reaction products thereof in the treatment layer and/or the phosphoric acid ester blend is from 1:1 to 1:100, preferably from 1:1.1 to 1:60, more preferably from 1:1.1 to 1:40, even more preferably from 1:1.1 to 1:20 and most preferably from 1:1.1 to 1:10.

The wording "molar ratio of the one or more phosphoric acid mono-ester and reaction products thereof to the one or more phosphoric acid di-ester and reaction products thereof" in the meaning of the present invention refers to the sum of the actual weight divided by the sum of the molecular weight of the phosphoric acid mono-ester molecules and/or the sum of the actual weight divided by the sum of the molecular weight of the phosphoric acid mono-ester molecules in the reaction products thereof to the sum of the actual weight divided by the sum of the molecular weight of the phosphoric acid di-ester molecules and/or the sum of the actual weight divided by the sum of the molecular weight of the phosphoric acid di-ester molecules in the reaction products thereof.

In one embodiment of the present invention, the phosphoric acid ester blend coated on at least a part of the surface of the calcium carbonate may further comprise one or more phosphoric acid tri-ester and/or phosphoric acid and/or reaction products thereof.

The term "phosphoric acid tri-ester" in the meaning of the present invention refers to an o-phosphoric acid molecule tri-esterified with three alcohol molecules selected from the same or different, unsaturated or saturated, branched or linear, aliphatic or aromatic alcohols having a total amount of carbon atoms from $C_6$ to $C_{30}$, preferably from $C_8$ to $C_{22}$, more preferably from $C_8$ to $C_{20}$ and most preferably from $C_8$ to $C_{18}$ in the alcohol substituent.

It is appreciated that the expression "one or more" phosphoric acid tri-ester means that one or more kinds of phosphoric acid tri-ester may be present on at least a part of the accessible surface area of the calcium carbonate.

Accordingly, it should be noted that the one or more phosphoric acid tri-ester may be one kind of phosphoric acid tri-ester. Alternatively, the one or more phosphoric acid tri-ester may be a mixture of two or more kinds of phosphoric acid tri-ester. For example, the one or more phosphoric acid tri-ester may be a mixture of two or three kinds of phosphoric acid tri-ester, like two kinds of phosphoric acid tri-ester.

In another embodiment the dried calcium carbonate-comprising material and/or partially dewatered calcium carbonate-comprising material can be treated with at least one mono-substituted succinic anhydride and/or at least one mono-substituted succinic acid and/or salty reaction product(s) thereof before or after the dewatering step g).

The expression "succinic anhydride", also called dihydro-2,5-furandione, succinic acid anhydride or succinyl oxide, has the molecular formula $C_4H_4O_3$ and is the acid anhydride of succinic acid.

The expression "mono-substituted" succinic anhydride in the meaning of the present invention refers to a succinic anhydride wherein a hydrogen atom is substituted by another substituent.

The expression "mono-substituted" succinic acid in the meaning of the present invention refers to a succinic acid wherein a hydrogen atom is substituted by another substituent.

It should be noted that the at least one mono-substituted succinic anhydride may be one kind of mono-substituted succinic anhydride. Alternatively, the at least one mono-substituted succinic anhydride may be a mixture of two or more kinds of mono-substituted succinic anhydride. For example, the at least one mono-substituted succinic anhydride may be a mixture of two or three kinds of mono-substituted succinic anhydride, like two kinds of mono-substituted succinic anhydride.

In one embodiment of the present invention, the at least one mono-substituted succinic anhydride is one kind of mono-substituted succinic anhydride.

It is appreciated that the at least one mono-substituted succinic anhydride represents a surface treatment agent and consists of succinic anhydride mono-substituted with a group selected from any linear, branched, aliphatic and cyclic group having a total amount of carbon atoms from C2 to C30 in the substituent.

In one embodiment of the present invention, the at least one mono-substituted succinic anhydride consists of succinic anhydride mono-substituted with a group selected from a linear, branched, aliphatic and cyclic group having a total amount of carbon atoms from C3 to C20 in the substituent. For example, the at least one mono-substituted succinic anhydride consists of succinic anhydride mono-substituted with a group selected from a linear, branched, aliphatic and cyclic group having a total amount of carbon atoms from C4 to C18 in the substituent.

In one embodiment of the present invention, the at least one mono-substituted succinic anhydride consists of succinic anhydride mono-substituted with one group being a linear and aliphatic group having a total amount of carbon atoms from C2 to C30, preferably from C3 to C20 and most preferably from C4 to C18 in the substituent. Additionally or alternatively, the at least one mono-substituted succinic anhydride consists of succinic anhydride mono-substituted with one group being a branched and aliphatic group having a total amount of carbon atoms from C2 to C30, preferably from C3 to C20 and most preferably from C4 to C18 in the substituent.

Thus, it is preferred that the at least one mono-substituted succinic anhydride consists of succinic anhydride mono-substituted with one group being a linear or branched, alkyl group having a total amount of carbon atoms from C2 to C30, preferably from C3 to C20 and most preferably from C4 to C18 in the substituent.

For example, the at least one mono-substituted succinic anhydride consists of succinic anhydride mono-substituted with one group being a linear alkyl group having a total amount of carbon atoms from C2 to C30, preferably from C3 to C20 and most preferably from C4 to C18 in the substituent. Additionally or alternatively, the at least one mono-substituted succinic anhydride consists of succinic anhydride mono-substituted with one group being a branched alkyl group having a total amount of carbon atoms from C2 to C30, preferably from C3 to C20 and most preferably from C4 to C18 in the substituent.

The term "alkyl" in the meaning of the present invention refers to a linear or branched, saturated organic compound composed of carbon and hydrogen. In other words, "alkyl mono-substituted succinic anhydrides" are composed of linear or branched, saturated hydrocarbon chains containing a pendant succinic anhydride group.

In one embodiment of the present invention, the at least one mono-substituted succinic anhydride is at least one linear or branched alkyl mono-substituted succinic anhydride. For example, the at least one alkyl mono-substituted succinic anhydride is selected from the group comprising ethylsuccinic anhydride, propylsuccinic anhydride, butylsuccinic anhydride, triisobutyl succinic anhydride, pentylsuccinic anhydride, hexylsuccinic anhydride, heptylsuccinic anhydride, octylsuccinic anhydride, nonylsuccinic anhydride, decyl succinic anhydride, dodecyl succinic anhydride, hexadecanyl succinic anhydride, octadecanyl succinic anhydride, and mixtures thereof.

Accordingly, it is appreciated that e.g. the term "butylsuccinic anhydride" comprises linear and branched butylsuccinic anhydride(s). One specific example of linear butylsuccinic anhydride(s) is n-butylsuccinic anhydride. Specific examples of branched butylsuccinic anhydride(s) are isobutylsuccinic anhydride, sec-butylsuccinic anhydride and/or tert-butylsuccinic anhydride.

Furthermore, it is appreciated that e.g. the term "hexadecanyl succinic anhydride" comprises linear and branched hexadecanyl succinic anhydride(s). One specific example of linear hexadecanyl succinic anhydride(s) is n-hexadecanyl succinic anhydride. Specific examples of branched hexadecanyl succinic anhydride(s) are 14-methylpentadecanyl succinic anhydride, 13-methylpentadecanyl succinic anhydride, 12-methylpentadecanyl succinic anhydride, 11-methylpentadecanyl succinic anhydride, 10-methylpentadecanyl succinic anhydride, 9-methylpentadecanyl succinic anhydride, 8-methylpentadecanyl succinic anhydride, 7-methylpentadecanyl succinic anhydride, 6-methylpentadecanyl succinic anhydride, 5-methylpentadecanyl succinic anhydride, 4-methylpentadecanyl succinic anhydride, 3-methylpentadecanyl succinic anhydride, 2-methylpentadecanyl succinic anhydride, 1-methylpentadecanyl succinic anhydride, 13-ethylbutadecanyl succinic anhydride, 12-ethylbutadecanyl succinic anhydride, 11-ethylbutadecanyl succinic anhydride, 10-ethylbutadecanyl succinic anhydride, 9-ethylbutadecanyl succinic anhydride, 8-ethylbutadecanyl succinic anhydride, 7-ethylbutadecanyl succinic anhydride, 6-ethylbutadecanyl succinic anhydride, 5-ethylbutadecanyl succinic anhydride, 4-ethylbutadecanyl succinic anhydride, 3-ethylbutadecanyl succinic anhydride, 2-ethylbutadecanyl succinic anhydride, 1-ethylbutadecanyl succinic anhydride, 2-butyldodecanyl succinic anhydride, 1-hexyldecanyl succinic anhydride, 1-hexyl-2-decanyl succinic anhydride, 2-hexyldecanyl succinic anhydride, 6,12-dimethylbutadecanyl succinic anhydride, 2,2-diethyldodecanyl succinic anhydride, 4,8,12-trimethyltridecanyl succinic anhydride, 2,2,4,6,8-pentamethylundecanyl succinic anhydride, 2-ethyl-4-methyl-2-(2-methylpentyl)-heptyl succinic anhydride and/or 2-ethyl-4,6-dimethyl-2-propylnonyl succinic anhydride.

Furthermore, it is appreciated that e.g. the term "octadecanyl succinic anhydride" comprises linear and branched octadecanyl succinic anhydride(s). One specific example of linear octadecanyl succinic anhydride(s) is n-octadecanyl succinic anhydride. Specific examples of branched hexadecanyl succinic anhydride(s) are 16-methylheptadecanyl succinic anhydride, 15-methylheptadecanyl succinic anhydride, 14-methylheptadecanyl succinic anhydride, 13-methylheptadecanyl succinic anhydride, 12-methylheptadecanyl succinic anhydride, 11-methylheptadecanyl succinic anhydride, 10-methylheptadecanyl succinic anhydride, 9-methylheptadecanyl succinic anhydride, 8-methylheptadecanyl succinic anhydride, 7-methylheptadecanyl succinic anhydride, 6-methylheptadecanyl succinic anhydride, 5-methylheptadecanyl succinic anhydride, 4-methylheptadecanyl succinic anhydride, 3-methylheptadecanyl succinic anhydride, 2-methylheptadecanyl succinic anhydride, 1-methylheptadecanyl succinic anhydride, 14-ethylhexadecanyl succinic anhydride, 13-ethylhexadecanyl succinic anhydride, 12-ethylhexadecanyl succinic anhydride, 11-ethylhexadecanyl succinic anhydride, 10-ethylhexadecanyl succinic anhydride, 9-ethylhexadecanyl succinic anhydride, 8-ethylhexadecanyl succinic anhydride, 7-ethylhexadecanyl succinic anhydride, 6-ethylhexadecanyl succinic anhydride, 5-ethylhexadecanyl succinic anhydride, 4-ethylhexadecanyl succinic anhydride, 3-ethylhexadecanyl succinic anhydride, 2-ethylhexadecanyl succinic anhydride, 1-ethylhexadecanyl succinic anhydride, 2-hexyldodecanyl succinic anhydride, 2-heptylundecanyl succinic anhydride, iso-octadecanyl succinic anhydride and/or 1-octyl-2-decanyl succinic anhydride.

In one embodiment of the present invention, the at least one alkyl mono-substituted succinic anhydride is selected from the group comprising butylsuccinic anhydride, hexylsuccinic anhydride, heptylsuccinic anhydride, octylsuccinic anhydride, hexadecanyl succinic anhydride, octadecanyl succinic anhydride, and mixtures thereof.

In one embodiment of the present invention, the at least one mono-substituted succinic anhydride is one kind of alkyl mono-substituted succinic anhydride. For example, the one alkyl mono-substituted succinic anhydride is butylsuccinic anhydride. Alternatively, the one alkyl mono-substituted succinic anhydride is hexylsuccinic anhydride. Alternatively, the one alkyl mono-substituted succinic anhydride is heptylsuccinic anhydride or octylsuccinic anhydride. Alternatively, the one alkyl mono-substituted succinic anhydride is hexadecanyl succinic anhydride. For example, the one alkyl mono-substituted succinic anhydride is linear hexadecanyl succinic anhydride such as n-hexadecanyl succinic anhydride or branched hexadecanyl succinic anhydride such as 1-hexyl-2-decanyl succinic anhydride. Alternatively, the one alkyl mono-substituted succinic anhydride is octadecanyl succinic anhydride. For example, the one alkyl mono-substituted succinic anhydride is linear octadecanyl succinic anhydride such as n-octadecanyl succinic anhydride or branched octadecanyl succinic anhydride such as iso-octadecanyl succinic anhydride or 1-octyl-2-decanyl succinic anhydride.

In one embodiment of the present invention, the one alkyl mono-substituted succinic anhydride is butylsuccinic anhydride such as n-butylsuccinic anhydride.

In one embodiment of the present invention, the at least one mono-substituted succinic anhydride is a mixture of two or more kinds of alkyl mono-substituted succinic anhydrides. For example, the at least one mono-substituted succinic anhydride is a mixture of two or three kinds of alkyl mono-substituted succinic anhydrides.

In one embodiment of the present invention, the at least one mono-substituted succinic anhydride consists of succinic anhydride mono-substituted with one group being a linear or branched alkenyl group having a total amount of carbon atoms from C2 to C30, preferably from C3 to C20 and most preferably from C4 to C18 in the substituent.

The term "alkenyl" in the meaning of the present invention refers to a linear or branched, unsaturated organic compound composed of carbon and hydrogen. Said organic compound further contains at least one double bond in the substituent, preferably one double bond. In other words, "alkenyl mono-substituted succinic anhydrides" are composed of linear or branched, unsaturated hydrocarbon chains containing a pendant succinic anhydride group. It is appreciated that the term "alkenyl" in the meaning of the present invention includes the cis and trans isomers.

In one embodiment of the present invention, the at least one mono-substituted succinic anhydride is at least one linear or branched alkenyl mono-substituted succinic anhydride. For example, the at least one alkenyl mono-substituted succinic anhydride is selected from the group comprising ethenylsuccinic anhydride, propenylsuccinic anhydride, butenylsuccinic anhydride, triisobutenyl succinic anhydride, pentenylsuccinic anhydride, hexenylsuccinic anhydride, heptenylsuccinic anhydride, octenylsuccinic anhydride, nonenylsuccinic anhydride, decenyl succinic anhydride, dodecenyl succinic anhydride, hexadecenyl succinic anhydride, octadecenyl succinic anhydride, and mixtures thereof.

Accordingly, it is appreciated that e.g. the term "hexadecenyl succinic anhydride" comprises linear and branched hexadecenyl succinic anhydride(s). One specific example of linear hexadecenyl succinic anhydride(s) is n-hexadecenyl succinic anhydride such as 14-hexadecenyl succinic anhydride, 13-hexadecenyl succinic anhydride, 12-hexadecenyl succinic anhydride, 11-hexadecenyl succinic anhydride, 10-hexadecenyl succinic anhydride, 9-hexadecenyl succinic anhydride, 8-hexadecenyl succinic anhydride, 7-hexadecenyl succinic anhydride, 6-hexadecenyl succinic anhydride, 5-hexadecenyl succinic anhydride, 4-hexadecenyl succinic anhydride, 3-hexadecenyl succinic anhydride and/or 2-hexadecenyl succinic anhydride. Specific examples of branched hexadecenyl succinic anhydride(s) are 14-methyl-9-pentadecenyl succinic anhydride, 14-methyl-2-pentadecenyl succinic anhydride, 1-hexyl-2-decenyl succinic anhydride and/or iso-hexadecenyl succinic anhydride.

Furthermore, it is appreciated that e.g. the term "octadecenyl succinic anhydride" comprises linear and branched octadecenyl succinic anhydride(s). One specific example of linear octadecenyl succinic anhydride(s) is n-octadecenyl succinic anhydride such as 16-octadecenyl succinic anhydride, 15-octadecenyl succinic anhydride, 14-octadecenyl succinic anhydride, 13-octadecenyl succinic anhydride, 12-octadecenyl succinic anhydride, 11-octadecenyl succinic anhydride, 10-octadecenyl succinic anhydride, 9-octadecenyl succinic anhydride, 8-octadecenyl succinic anhydride, 7-octadecenyl succinic anhydride, 6-octadecenyl succinic anhydride, 5-octadecenyl succinic anhydride, 4-octadecenyl succinic anhydride, 3-octadecenyl succinic anhydride and/or 2-octadecenyl succinic anhydride. Specific examples of branched octadecenyl succinic anhydride(s) are 16-methyl-9-heptadecenyl succinic anhydride, 16-methyl-7-heptadecenyl succinic anhydride, 1-octyl-2-decenyl succinic anhydride and/or iso-octadecenyl succinic anhydride.

In one embodiment of the present invention, the at least one alkenyl mono-substituted succinic anhydride is selected from the group comprising hexenylsuccinic anhydride, octenylsuccinic anhydride, hexadecenyl succinic anhydride, octadecenyl succinic anhydride, and mixtures thereof.

In one embodiment of the present invention, the at least one mono-substituted succinic anhydride is one alkenyl mono-substituted succinic anhydride. For example, the one alkenyl mono-substituted succinic anhydride is hexenylsuccinic anhydride. Alternatively, the one alkenyl mono-substituted succinic anhydride is octenylsuccinic anhydride.

Alternatively, the one alkenyl mono-substituted succinic anhydride is hexadecenyl succinic anhydride. For example, the one alkenyl mono-substituted succinic anhydride is linear hexadecenyl succinic anhydride such as n-hexadecenyl succinic anhydride or branched hexadecenyl succinic anhydride such as 1-hexyl-2-decenyl succinic anhydride. Alternatively, the one alkenyl mono-substituted succinic anhydride is octadecenyl succinic anhydride. For example, the one alkyl mono-substituted succinic anhydride is linear octadecenyl succinic anhydride such as n-octadecenyl succinic anhydride or branched octadecenyl succinic anhydride such iso-octadecenyl succinic anhydride, or 1-octyl-2-decenyl succinic anhydride.

In one embodiment of the present invention, the one alkenyl mono-substituted succinic anhydride is linear octadecenyl succinic anhydride such as n-octadecenyl succinic anhydride. In another embodiment of the present invention, the one alkenyl mono-substituted succinic anhydride is linear octenylsuccinic anhydride such as n-octenylsuccinic anhydride.

If the at least one mono-substituted succinic anhydride is one alkenyl mono-substituted succinic anhydride, it is appreciated that the one alkenyl mono-substituted succinic anhydride is present in an amount of ≥95 wt.-% and preferably of ≥96.5 wt.-%, based on the total weight of the at least one mono-substituted succinic anhydride.

In one embodiment of the present invention, the at least one mono-substituted succinic anhydride is a mixture of two or more kinds of alkenyl mono-substituted succinic anhydrides. For example, the at least one mono-substituted succinic anhydride is a mixture of two or three kinds of alkenyl mono-substituted succinic anhydrides.

If the at least one mono-substituted succinic anhydride is a mixture of two or more kinds of alkenyl mono-substituted succinic anhydrides, one alkenyl mono-substituted succinic anhydride is linear or branched octadecenyl succinic anhydride, while each further alkenyl mono-substituted succinic anhydride is selected from ethenylsuccinic anhydride, propenyl succinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof. For example, the at least one mono-substituted succinic anhydride is a mixture of two or more kinds of alkenyl mono-substituted succinic anhydrides, wherein one alkenyl mono-substituted succinic anhydride is linear octadecenyl succinic anhydride and each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof. Alternatively, the at least one mono-substituted succinic anhydride is a mixture of two or more kinds of alkenyl mono-substituted succinic anhydrides, wherein one alkenyl mono-substituted succinic anhydride is branched octadecenyl succinic anhydride and each further alkenyl mono-substituted succinic anhydride is selected from ethenylsuccinic anhydride, propenylsuccinic anhydride, butenylsuccinic anhydride, pentenylsuccinic anhydride, hexenylsuccinic anhydride, heptenylsuccinic anhydride, nonenylsuccinic anhydride, hexadecenyl succinic anhydride and mixtures thereof.

For example, the at least one mono-substituted succinic anhydride is a mixture of two or more kinds of alkenyl mono-substituted succinic anhydrides comprising one or more hexadecenyl succinic anhydride, like linear or branched hexadecenyl succinic anhydride(s), and one or more octadecenyl succinic anhydride, like linear or branched octadecenyl succinic anhydride(s).

In one embodiment of the present invention, the at least one mono-substituted succinic anhydride is a mixture of two or more kinds of alkenyl mono-substituted succinic anhydrides comprising linear hexadecenyl succinic anhydride(s) and linear octadecenyl succinic anhydride(s). Alternatively, the at least one mono-substituted succinic anhydride is a mixture of two or more kinds of alkenyl mono-substituted succinic anhydrides comprising branched hexadecenyl succinic anhydride(s) and branched octadecenyl succinic anhydride(s). For example, the one or more hexadecenyl succinic anhydride is linear hexadecenyl succinic anhydride like n-hexadecenyl succinic anhydride and/or branched hexadecenyl succinic anhydride like 1-hexyl-2-decenyl succinic anhydride. Additionally or alternatively, the one or more octadecenyl succinic anhydride is linear octadecenyl succinic anhydride like n-octadecenyl succinic anhydride and/or branched octadecenyl succinic anhydride like iso-octadecenyl succinic anhydride and/or 1-octyl-2-decenyl succinic anhydride.

If the at least one mono-substituted succinic anhydride is a mixture of two or more kinds of alkenyl mono-substituted succinic anhydrides, it is appreciated that one alkenyl mono-substituted succinic anhydride is present in an amount of from 20 to 60 wt.-% and preferably of from 30 to 50 wt.-%, based on the total weight of the at least one mono-substituted succinic anhydride provided.

For example, if the at least one mono-substituted succinic anhydride is a mixture of two or more kinds of alkenyl mono-substituted succinic anhydrides comprising one or more hexadecenyl succinic anhydride(s), like linear or branched hexadecenyl succinic anhydride(s), and one or more octadecenyl succinic anhydride(s), like linear or branched hexadecenyl succinic anhydride(s), it is preferred that the one or more octadecenyl succinic anhydride(s) is present in an amount of from 20 to 60 wt.-% and preferably of from 30 to 50 wt.-%, based on the total weight of the at least one mono-substituted succinic anhydride.

It is also appreciated that the at least one mono-substituted succinic anhydride may be a mixture of at least one alkyl mono-substituted succinic anhydrides and at least one alkenyl mono-substituted succinic anhydrides.

If the at least one mono-substituted succinic anhydride is a mixture of at least one alkyl mono-substituted succinic anhydrides and at least one alkenyl mono-substituted succinic anhydrides, it is appreciated that the alkyl substituent of the of at least one alkyl mono-substituted succinic anhydrides and the alkenyl substituent of the of at least one alkenyl mono-substituted succinic anhydrides are preferably the same. For example, the at least one mono-substituted succinic anhydride is a mixture of ethylsuccinic anhydride and ethenylsuccinic anhydride. Alternatively, the at least one mono-substituted succinic anhydride is a mixture of propylsuccinic anhydride and propenylsuccinic anhydride. Alternatively, the at least one mono-substituted succinic anhydride is a mixture of butylsuccinic anhydride and butenylsuccinic anhydride. Alternatively, the at least one mono-substituted succinic anhydride is a mixture of triisobutyl succinic anhydride and triisobutenyl succinic anhydride. Alternatively, the at least one mono-substituted succinic anhydride is a mixture of pentylsuccinic anhydride and pentenylsuccinic anhydride. Alternatively, the at least one mono-substituted succinic anhydride is a mixture of hexylsuccinic anhydride and hexenylsuccinic anhydride. Alternatively, the at least one mono-substituted succinic anhydride is a mixture of heptylsuccinic anhydride and heptenylsuccinic anhydride. Alternatively, the at least one mono-substituted succinic anhydride is a mixture of octylsuccinic anhydride and octenylsuccinic anhydride. Alternatively, the at least one mono-substituted succinic anhydride is a mixture of nonylsuccinic anhydride and nonenylsuccinic anhydride. Alternatively, the at least one mono-substituted succinic anhydride is a mixture of decyl succinic anhydride and decenyl succinic anhydride. Alternatively, the at least one mono-substituted succinic anhydride is a mixture of dodecyl succinic anhydride and dodecenyl succinic anhydride. Alternatively, the at least one mono-substituted succinic anhydride is a mixture of hexadecanyl succinic anhydride and hexadecenyl succinic anhydride. For example, the at least one mono-substituted succinic anhydride is a mixture of linear hexadecanyl succinic anhydride and linear hexadecenyl succinic anhydride or a mixture of branched hexadecanyl succinic anhydride and branched hexadecenyl succinic anhydride. Alternatively, the at least one mono-substituted succinic anhydride is a mixture of octadecanyl succinic anhydride and octadecenyl succinic anhydride. For example, the at least one mono-substituted succinic anhydride is a mixture of linear octadecanyl succinic anhydride and linear octadecenyl succinic anhydride or a mixture of branched octadecanyl succinic anhydride and branched octadecenyl succinic anhydride.

In one embodiment of the present invention, the at least one mono-substituted succinic anhydride is a mixture of nonylsuccinic anhydride and nonenylsuccinic anhydride.

If the at least one mono-substituted succinic anhydride is a mixture of at least one alkyl mono-substituted succinic anhydrides and at least one alkenyl mono-substituted succinic anhydrides, the weight ratio between the at least one alkyl mono-substituted succinic anhydride and the at least one alkenyl mono-substituted succinic anhydride is between 90:10 and 10:90 (wt.-%/wt.-%). For example, the weight ratio between the at least one alkyl mono-substituted succinic anhydride and the at least one alkenyl mono-substituted succinic anhydride is between 70:30 and 30:70 (wt.-%/wt.-%) or between 60:40 and 40:60.

It is appreciated that the expression "at least one" mono-substituted succinic acid means that one or more kinds of mono-substituted succinic acid may be provided in the process of the present invention.

Accordingly, it should be noted that the at least one mono-substituted succinic acid may be one kind of mono-substituted succinic acid. Alternatively, the at least one mono-substituted succinic acid may be a mixture of two or more kinds of mono-substituted succinic acid. For example, the at least one mono-substituted succinic acid may be a mixture of two or three kinds of mono-substituted succinic acid, like two kinds of mono-substituted succinic acid.

In one embodiment of the present invention, the at least one mono-substituted succinic acid is one kind of mono-substituted succinic acid.

It is appreciated that the at least one mono-substituted succinic acid represents a surface treatment agent and consists of succinic acid mono-substituted with a group selected from any linear, branched, aliphatic and cyclic group having a total amount of carbon atoms from C2 to C30 in the substituent.

In one embodiment of the present invention, the at least one mono-substituted succinic acid consists of succinic acid mono-substituted with a group selected from a linear, branched, aliphatic and cyclic group having a total amount of carbon atoms from C3 to C20 in the substituent. For example, the at least one mono-substituted succinic acid consists of succinic acid mono-substituted with a group selected from a linear, branched, aliphatic and cyclic group having a total amount of carbon atoms from C4 to C18 in the substituent.

It is appreciated that the at least one mono-substituted succinic anhydride and the at least one mono-substituted succinic acid may comprise the same or different substituent.

In one embodiment of the present invention, the succinic acid molecule of the at least one mono-substituted succinic acid and the succinic anhydride molecule of the at least one mono-substituted succinic anhydride are mono-substituted with the same group selected from any linear, branched, aliphatic and cyclic group having a total amount of carbon atoms from C2 to C30, preferably from C3 to C20 and most preferably from C4 to C18 in the substituent.

If the at least one mono-substituted succinic anhydride is provided in combination with at least one mono-substituted succinic acid, the at least one mono-substituted succinic acid is present in an amount of ≤10 mol.-%, based on the molar sum of the at least one mono-substituted succinic anhydride and the at least one mono-substituted succinic acid. For example, the at least one mono-substituted succinic acid is present in an amount of ≤5 mol.-%, preferably of ≤2.5 mol.-% and most preferably of ≤1 mol.-%, based on the molar sum of the at least one mono-substituted succinic anhydride and the at least one mono-substituted succinic acid.

According to another embodiment of present invention it is preferred that the partially dewatered calcium carbonate-comprising material and/or dried calcium carbonate-comprising material is treated before or after dewatering and optionally drying step g) with the at least one saturated aliphatic linear or branched carboxylic acid to obtain a hydrophobized calcium carbonate-comprising material. For example, the partially dewatered calcium carbonate-comprising material or the dried calcium carbonate-comprising material is treated before or after dewatering or drying step f) with the at least one saturated aliphatic linear or branched carboxylic acid to obtain a hydrophobized calcium carbonate-comprising material.

In one embodiment of the present invention, the partially dewatered calcium carbonate-comprising material or dried calcium carbonate-comprising material is treated before dewatering or drying step g) with the at least one saturated aliphatic linear or branched carboxylic acid to obtain a hydrophobized calcium carbonate-comprising material. Preferably, the partially dewatered calcium carbonate-comprising material is treated before dewatering step g) with the at least one saturated aliphatic linear or branched carboxylic acid to obtain a hydrophobized calcium carbonate-comprising material.

Alternatively, the partially dewatered calcium carbonate-comprising material and/or the dried calcium carbonate-comprising material is treated after dewatering or drying step g) with the at least one saturated aliphatic linear or branched carboxylic acid to obtain a hydrophobized calcium carbonate-comprising material.

In one embodiment of the present invention, the partially dewatered calcium carbonate-comprising material or the dried calcium carbonate-comprising material is treated after dewatering and optional drying step g) with the at least one saturated aliphatic linear or branched carboxylic acid to obtain a hydrophobized calcium carbonate-comprising material. For example, the dried calcium carbonate-comprising material is treated after drying step g) with the at least one saturated aliphatic linear or branched carboxylic acid to obtain a hydrophobized calcium carbonate-comprising material.

Additionally or alternatively, the partially dewatered calcium carbonate-comprising material can be treated with at least one dispersing agent after dewatering step g). For example, the partially dewatered calcium carbonate-comprising material to be treated with the at least one dispersing agent may be in the form of an aqueous suspension having solids content of ≤40.0 wt.-%, such as from 5.0 to 40.0 wt.-%, based on the total weight of the aqueous suspension. Alternatively, the partially dewatered calcium carbonate-comprising material to be treated with the at least one dispersing agent may be in the form of a filter cake having solids content of from 50.0 to 85.0 wt.-%, based on the total weight of the filter cake.

Dispersing agents suitable for dispersing such partially dewatered calcium carbonate-comprising materials are well known to the skilled person. For example, the dispersing agent can be selected from sodium and/or potassium and/or ammonium salts of at least partly neutralized homopolymers or copolymers of acrylic acid or maleic acid, such as sodium polyacrylate having a molecular weight $M_w$ of from 4 000 to 10 000 g/mol, preferably from 4 000 to 8 000 g/mol and most preferably of about 6 000 g/mol, sodium hydrogen phosphate, carboxymethylcellulose (CMC), methyl methacrylate, steric, comb polymers and mixtures thereof. In one embodiment of the present invention, the dispersing agent is a mixture of sodium polyacrylate and sodium hydrogen phosphate.

If the partially dewatered calcium carbonate-comprising material is treated with a dispersing agent, the dispersing agent is preferably present in a total amount of from 0.05 to 2.0 wt.-%, more preferably from 0.1 to 1.5 wt.-% and most preferably from 0.3 to 1.0 wt.-%, based on the total dry weight of the at least one calcium carbonate-comprising material. It is to be noted that the amount of the dispersing agent is calculated as active material on dry matter calcium carbonate-comprising material.

Additionally or alternatively, the partially dewatered calcium carbonate-comprising material and/or the dried calcium carbonate-comprising material may be re-diluted with water such as to obtain an aqueous suspension comprising the at least one calcium carbonate-comprising material.

If the partially dewatered calcium carbonate-comprising material and/or the dried calcium carbonate-comprising material is re-diluted with water, the obtained aqueous suspension preferably has solids content from 10.0 to 80.0 wt.-%, preferably from 15.0 to 79.0 wt.-%, and most preferably from 20.0 to 78.0 wt.-%, based on the total weight of the aqueous suspension.

In one embodiment of the present invention, the partially dewatered calcium carbonate-comprising material and/or the dried calcium carbonate-comprising material is re-diluted with water such as to obtain an aqueous suspension having solids content from 50.0 to 80.0 wt.-%, preferably from 60.0 to 80.0 wt.-%, and most preferably from 65.0 to 78.0 wt.-%, based on the total weight of the aqueous suspension.

For example, the partially dewatered calcium carbonate-comprising material and/or the dried calcium carbonate-comprising material can be re-diluted with water such as to obtain an aqueous suspension having solids content from 65.0 to 75.0 wt.-%, based on the total weight of the aqueous suspension.

Thus, it is appreciated that the aqueous suspension obtained by re-diluting the partially dewatered calcium carbonate-comprising material and/or the dried calcium carbonate-comprising material may comprise at least one saturated aliphatic linear or branched carboxylic acid or is free of saturated aliphatic linear or branched carboxylic acids. Accordingly, the calcium carbonate-comprising material can be a hydrophobized calcium carbonate-comprising material, i.e. obtained by treating the at least one calcium carbonate-comprising material with at least one saturated aliphatic linear or branched carboxylic acid.

The calcium carbonate material obtained by the process according to the present invention has a moisture-pick up susceptibility of 0.01 to 1 mg/g, preferably 0.1 to 0.9 mg/g and more preferably 0.2 to 0.8 mg/g.

In one embodiment of the present invention, the aqueous suspension obtained by re-diluting the partially dewatered calcium carbonate-comprising material may comprise a dispersing agent or is free of dispersing agents. Accordingly, the calcium carbonate-comprising material can be a dispersed or undispersed material.

In one embodiment of the present invention, the calcium carbonate-comprising material obtained after process step g) is a dispersed material.

The calcium carbonate-comprising material obtained by the instant process is characterized by a specific narrow particle size distribution, i.e. a steepness factor expressed by the ratio of particles having an average particle size $d_{80}$ value to particles having an average particle size $d_{20}$ value [$d_{80}/d_{20}$].

It is appreciated that the at least one calcium carbonate-comprising material obtained by the instant process after step f) has a ratio of particles having an average particle size $d_{80}$ value to particles having an average particle size $d_{20}$ value [$d_{80}/d_{20}$] in the range from 1.5 to 4.

In one embodiment of the present invention, the at least one calcium carbonate-comprising material obtained by the instant process after step f) has a ratio of particles having an average particle size $d_{80}$ value to particles having an average particle size $d_{20}$ value [$d_{80}/d_{20}$] of from 1.5 to 4.0, preferably from 1.7 to 3.50 and most preferably from 2.2 to 3.4.

It is to be noted that the steepness factor is not changing if optional process step g) is implemented in the process and thus the at least one calcium carbonate-comprising material obtained after optional process step g) also has a steepness factor as outlined above, i.e. a ratio of particles having an average particle size $d_{80}$ value to particles having an average particle size $d_{20}$ value [$d_{80}/d_{20}$] of ≤4.1, of from 1.5 to 4.0, preferably from 1.7 to 3.50 and most preferably from 2.2 to 3.4.

Preferably, the at least one calcium carbonate-comprising material obtained by the instant process has a lower ratio of particles having an average particle size $d_{80}$ value to particles having an average particle size $d_{20}$ value [$d_{80}/d_{20}$] than a calcium carbonate-comprising material that is obtained by wet-grinding the same suspension of step a) to similar particle size but without pre-heating step b) and/or contacting step d) and/or storing step/f).

It is further appreciated that the at least one calcium carbonate-comprising material obtained by the instant process after step f) has a low BET specific surface area. Preferably, the at least one calcium carbonate-containing material has a BET specific surface area of ≤15.0 m²/g, preferably in the range from 1.0 to 15.0 m²/g, more preferably from 2.0 to 14.0 m²/g, and even more preferably from 2.5 to 13.0 m²/g and most preferably from 2.5 to 4 m²/g.

It is to be noted that the BET specific surface area of the at least one calcium carbonate-comprising material obtained by the instant process is lower than the BET specific surface area of at least one calcium carbonate-comprising material that is obtained by wet-grinding the same suspension of step a) to similar particle size but without pre-heating step b) and contacting step d) or storing step f).

The favourable characteristics of the at least one calcium carbonate-comprising material obtained by the instant process, can be also expressed by the normalized SSA which can be calculated by the ratio of BET specific surface area to the weight median particle size diameter $d_{50}$ [SSA/$d_{50}$]. The at least one calcium carbonate-comprising material obtained by the instant process after step f) preferably has a normalized SSA [SSA/$d_{50}$] of ≤15.0*$10^6$ m/g, preferably in the range from 0.5 to 10*$10^6$ m/g, more preferably in the range from 0.9 to 7*$10^6$ m/g and most preferably in the range from 1.5 to 4.5*$10^6$ m/g.

Additionally or alternatively, the at least one calcium carbonate-comprising material obtained after optional process step g) also has a normalized SSA as outlined above, i.e. a normalized SSA [SSA/$d_{50}$] of ≤15.0*$10^6$ m/g, preferably in the range from 0.5 to 10.0*$10^6$ m/g, more preferably in the range from 0.9 to 7.0*$10^6$ m/g and most preferably in the range from 1.5 to 4.5*$10^6$ m/g.

The favourable characteristics of the at least one calcium carbonate-comprising material obtained by the instant process, can be also expressed by the deviation of the average measured weight median particle diameter $d_{50}$ from the diameter of an ideal sphere with the same specific surface area. The diameter dp of an ideal sphere with the same specific surface area can be calculated according to following formula (1).

$$dp = 6/\rho \cdot SSA \quad (1)$$

wherein dp is the diameter of an ideal sphere with the same specific surface area;
$\rho$ is the density of calcium carbonate (2.7 kg/m$^3$); and
SSA is the BET-specific surface area determined according to ISO 4652 as described in the experimental part.

Formula (1) is derived from formula (2) to (4).

$$A = \pi \cdot dp^2 \quad (2)$$

$$V = \pi \cdot dp^3/6 \quad (3)$$

$$SSA = A/\rho \cdot V \quad (4)$$

wherein A is the surface area and V is the surface volume.

The deviation of the measured $d_{50}$ from the diameter dp of an ideal sphere with the same specific surface area of the calcium carbonate-comprising material obtained after step f) or step g) is preferably between 100 and 200%, more preferably between 120 and 180% and most preferably between 130 and 165% relative to the diameter of the ideal sphere with the same specific surface area.

In one embodiment of the present invention, the at least one calcium carbonate-comprising material obtained by the instant process has a lower normalized SSA than a calcium carbonate-comprising material that is obtained by wet-grinding the same suspension of step a) to similar particle size but without pre-heating step b) and contacting step d) and/or storing step f).

In view of the good results obtained, a further aspect of the present invention is directed to a calcium carbonate-comprising material having a ratio of particles having an average particle size $d_{80}$ value to particles having an average particle size $d_{20}$ value [$d_{80}/d_{20}$] in the range from 1.5 to 4, preferably 1.7 to 3.5 and more preferably 2.2 to 3.4. It is one requirement of the instant invention that the calcium carbonate-comprising material is obtained by a process as defined above, i.e. process steps a), b), c), d), e), f) and optional process step g).

It view of the applications or uses as given below it is preferred that the calcium carbonate-comprising material is in the form of a partially dewatered or dried calcium carbonate-comprising material. In particular, the partially dewatered or dried calcium carbonate-comprising material is obtained by drying or dewatering the aqueous suspension comprising the at least one calcium carbonate-comprising material obtained in step f) of the process of the present invention. Optionally, the partially dewatered or dried calcium carbonate-comprising material is further treated with at least one dispersing agent and re-diluted to obtain an aqueous suspension and/or treated with at least one saturated aliphatic linear or branched carboxylic acid or at least one mono-substituted succinic anhydride and/or at least one mono-substituted succinic acid and/or salty reaction product(s) thereof.

With regard to the definition of the aqueous suspension, the calcium carbonate-comprising material and preferred embodiments thereof, reference is made to the comments provided above when further discussing the aqueous suspension comprising the at least one calcium carbonate-comprising material obtained in step f) and optional process step g) of the process of the present invention.

In particular, aqueous suspensions comprising the calcium carbonate-comprising material and/or partially dewatered or dried calcium carbonate-comprising material, and optionally further treated with at least one dispersing agent and re-diluted to obtain an aqueous suspension and/or treated with at least one saturated aliphatic linear or branched carboxylic acid, according to the invention are characterized in that they contain the calcium carbonate-comprising material obtained by the process of the present invention. The particles of the calcium carbonate-comprising material according to the present invention are especially characterized in that they feature an improved or optimized narrow particle size distribution and low BET specific surface area in comparison to calcium carbonate-comprising materials prepared by processes of the prior art. In contrast to prior art processes, the foregoing is achieved by a less time-consuming heat-ageing step after wet-grinding but rather through wet-grinding a pre-heated aqueous suspension comprising at least one calcium carbonate-comprising material in the presence of at least one base. It is believed that such process results in a calcium carbonate-comprising material featuring an improved or optimized narrow particle size distribution and improved or optimized values for the BET specific surface area and thus imparting improved or optimized optical properties such as opacity and brightness and light scattering properties in paper products, or good mechanical and optical properties, like gloss, in polymer products comprising such material. As another advantage, the at least one calcium carbonate-comprising material obtained by the process of the present invention can be prepared in a simple way and with less time-consuming process steps.

Another third aspect of the present invention refers to a process for the preparation of an aqueous suspension comprising at least one calcium carbonate-comprising material, the process comprising the following steps:
a) providing a substantially dispersant-free aqueous suspension of at least one calcium carbonate-comprising material, and c) wet-grinding the suspension of step a) in at least one grinding step for obtaining an aqueous suspension of at least one wet ground calcium carbonate-comprising material, and d) contacting the aqueous suspension before and/or during and/or after wet-grinding step c), or before or during or after removal step e) with at least one base for obtaining an aqueous suspension having a pH measured at 25° C. of ≥9.0, and e) removal of at least a part of particles with a diameter >20 μm in the aqueous suspension of the at least one wet ground calcium carbonate comprising material, and f) storing the aqueous suspension obtained after contacting step d) or removal step e) at a temperature of from 70 to 140° C. for a period of time of 0.25 to 10 hours, for obtaining an aqueous suspension of at least one calcium carbonate-comprising material having a ratio of particles having an average particle size $d_{80}$ value to particles having an average particle size $d_{20}$ value $[d_{80}/d_{20}]$ in the range from 1.5 to 4, wherein the pH is kept >8.5 before, during and after steps a), c), d), e) and before and during step f).

In this embodiment an optional heating step can be carried out after the wet-grinding step c) and/or after the contacting step d).

It is to be understood that the following preferred embodiments relating to the inventive process of the third aspect also apply to the inventive use as claimed. Furthermore, the following preferred embodiments are described as aspects relating to said third aspect (aspect 3) of the present invention.

4. Process according to aspect 3 (the third aspect of the present invention), wherein the content of particles with a particle diameter <1 μm of the at least one calcium carbonate-comprising material provided in the aqueous suspension of step a) is between 30 to 90 wt.-%, preferably between 35 and 65 wt.-% and most preferably between 40 and 60 wt.-%, based on the weight of the at least one calcium carbonate-comprising material. The inventive process is especially suitable for the processing of relatively coarse starting materials.

5. Process according to aspect 3 or 4, wherein the at least one calcium carbonate-comprising material provided in the aqueous suspension of step a) is dolomite and/or a natural ground calcium carbonate (NGCC), such as one or more of marble, limestone and/or chalk.

6. Process according to any of aspects 3 to 5, wherein the aqueous suspension provided in step a) has a solids content of from 5.0 wt.-% to 60.0 wt.-%, preferably from 10.0 wt.-% to 55.0 wt.-% and most preferably from 15.0 wt.-% to 50.0 wt.-%, based on the total weight of the aqueous suspension.

7. Process according to any of aspects 3 to 6, wherein the aqueous suspension of step a) does not undergo any pre-heating step prior to wet-grinding step c).

8. Process according to any of aspects 3 to 7, wherein the contacting step d) is carried out after removal step e).

9. Process according to any of aspects 3 to 8, wherein the contacting step d) is carried out such that the obtained aqueous suspension has a pH measured at 25° C. of from 10.0 to 13.5 and preferably from 11.0 to 13.0.

10. Process according to any of aspects 3 to 9, wherein the at least one base in contacting step d) is a) added in an amount of ≥0.05 wt.-%, preferably of ≥0.1 wt.-%, more preferably of ≥0.2 wt.-% and most preferably of from 0.2 to 1.0 wt.-%, based on the total dry weight of the calcium carbonate-comprising material, and/or b) at least one alkali metal hydroxide selected from the group comprising lithium hydroxide, sodium hydroxide, potassium hydroxide and mixtures thereof and/or at least one earth alkali metal hydroxide selected from the group comprising magnesium hydroxide, calcium hydroxide and mixtures thereof.

11. Process according to any of aspects 3 to 10, wherein that the removal step e) is carried out by using a centrifuge, at least one sieve or a disc separator or mixtures thereof for removing >90 wt.-% of particles with a diameter >100 μm and >70 wt. % of particles with a diameter >20 μm, preferably for removing essentially all particles with a diameter >100 μm and >90 wt.-% of particles with a diameter >20 μm, based on the weight of at least one wet ground calcium carbonate comprising material.

12. Process according to any of aspects 3 to 11, wherein step f) of storing the aqueous suspension is carried out at a temperature of from 75 to 130° C. and most preferably from 80 to 95° C., and/or for a period of time of 0.1 to 7 hours, preferably 0.5 to 3.5 hours, more preferably 0.75 to 2.5 hours and most preferably 1 to 2 hours.

13. Process according to any of aspects 3 to 12, wherein the aqueous suspension stored in step f) has solids content of from 5.0 wt.-% to 60.0 wt.-%, preferably from 10.0 wt.-% to 55.0 wt.-%, more preferably from 15.0 wt.-% to 50.0 wt.-% and most preferably from 20.0 wt.-% to 50.0 wt.-%, based on the total weight of the aqueous suspension.

14. Process according to any of aspects 3 to 13, wherein the ratio of particles having an average particle size $d_{80}$ value to particles having an average particle size $d_{20}$ value $[d_{80}/d_{20}]$ of the at least one calcium carbonate-comprising material obtained after storing step f) is in the range from 1.7 to 3.5, preferably from 2.2 to 3.4.

15. Process according to any of aspects 3 to 14, wherein the process further comprises step g) of dewatering and optionally drying the aqueous suspension obtained in step e) to remove at least a portion of water to obtain a partially dewatered calcium carbonate-comprising material or to obtain a dried calcium carbonate-comprising material.

16. Process according to aspect 15, wherein the material obtained after step f) or step g) is deagglomerated, preferably in a pin-mill.

17. Process according to aspect 15 or 16, wherein the obtained material is heated to a temperature in the range from 60 to 150° C., preferably 70 to 130° C. and most preferably 80 to 110° C. to obtain a material with a total moisture content in the range from 0.05 to 0.2 wt.-%, preferably 0.01 to 0.1 wt.-% based on the total weight of the calcium carbonate-comprising material.

18. Process according to any of aspects 15 to 17, wherein, a) the partially dewatered calcium carbonate-comprising material is treated after dewatering step g) with at least one dispersing agent and re-diluted to obtain an aqueous suspension comprising a dispersed calcium carbonate-comprising material, and/or b) the partially dewatered calcium carbonate-comprising material and/or the dried calcium carbonate-comprising material is treated before or after dewatering or drying step g) with at least one saturated aliphatic linear or branched carboxylic acid and/or with at least one mono-substituted succinic anhydride and/or at least one mono-substituted succinic acid and/or salty reaction product(s) and/or with at least one phosphoric acid ester blend of one or more phosphoric acid mono-ester and/or reaction products thereof and one or more phosphoric acid di-ester and/or reaction products thereof to obtain a hydrophobized calcium carbonate-comprising material.

19. Process according to any of aspects 3 to 14, wherein the at least one calcium carbonate-comprising material obtained in step f) has
   a) a BET specific surface area of ≤15.0 m²/g, preferably in the range from 1.0 to 15.0 m²/g, more preferably from 2.0 to 14.0 m²/g, and most preferably from 2.5 to 13.0 m²/g, and/or
   b) a lower ratio of particles having an average particle size $d_{80}$ value to particles having an average particle size $d_{20}$ value $[d_{80}/d_{20}]$ than a calcium carbonate-comprising material that is obtained in an identical manner but without contacting step d) and/or storing step f).

20. Process according to any of aspects 15 to 18, wherein the at least one calcium carbonate-comprising material obtained in step g) has
   a) a BET specific surface area of ≤15.0 m²/g, preferably in the range from 1.0 to 15.0 m²/g, more preferably from 2.0 to 14.0 m²/g, and most preferably from 2.5 to 13.0 m²/g, and/or
   b) a lower ratio of particles having an average particle size $d_{80}$ value to particles having an average particle size $d_{20}$ value $[d_{80}/d_{20}]$ than a calcium carbonate-comprising material that is obtained in an identical manner but without contacting step d) and/or storing step f).

Furthermore, reference is made to the detailed description of process steps a), c), d), e), f) and g) provided herein above with respect to the process according to the first aspect of the present invention. It is emphasized that said detailed description of said process steps and the further preferred embodiments described therein also apply to the process according to the third aspect of the present invention.

Another 21th aspect of the present invention refers to a process for the preparation of an aqueous suspension comprising at least one calcium carbonate-comprising material, the process comprising the following steps:
   a) providing a substantially dispersant-free aqueous suspension of at least one calcium carbonate-comprising material, and
   b) pre-heating the suspension of step a) to a temperature of from 40 to 95° C. at ambient pressure, and
   c) wet-grinding the pre-heated suspension in at least one grinding step for obtaining an aqueous suspension of at least one wet ground calcium carbonate-comprising material, and
   e) removal of at least a part of the particles with a diameter >20 μm in the aqueous suspension of the at least one wet ground calcium carbonate comprising material, and
   f) storing the aqueous suspension obtained after removal step e) at a temperature of from 70 to 140° C. for a period of time of 0.25 to 8 hours, for obtaining an aqueous suspension of at least one calcium carbonate-comprising material having a ratio of particles having an average particle size $d_{80}$ value to particles having an average particle size $d_{20}$ value $[d_{80}/d_{20}]$ in the range from 1.5 to 4.0.

In this embodiment an optional heating step can be carried out after the wet-grinding step c).

It is to be understood that the following preferred embodiments relating to the inventive process of the 21th aspect also apply to the inventive use as claimed. Furthermore, the following preferred embodiments are described as aspects relating to said 21th aspect (aspect 21) of the present invention.

22. Process according to aspect 21 (the 21th aspect of the present invention), wherein the content of particles with a particle diameter <1 μm of the at least one calcium carbonate-comprising material provided in the aqueous suspension of step a) is between 30 to 90 wt.-%, preferably between 35 and 65 wt.-% and most preferably between 40 and 60 wt.-%, based on the weight of the at least one calcium carbonate-comprising material. The inventive process is especially suitable for the processing of relatively coarse starting materials.

23. Process according to aspect 21 or 22, wherein the at least one calcium carbonate-comprising material provided in the aqueous suspension of step a) is dolomite and/or a natural ground calcium carbonate (NGCC), such as one or more of marble, limestone and/or chalk.

24. Process according to any of aspects 21 to 23, wherein the aqueous suspension provided in step a) has a solids content of from 5.0 wt.-% to 60.0 wt.-%, preferably from 10.0 wt.-% to 55.0 wt.-% and most preferably from 15.0 wt.-% to 50.0 wt.-%, based on the total weight of the aqueous suspension.

25. Process according to any of aspects 21 to 24, wherein the aqueous suspension of step a) does not undergo any pre-heating step prior to wet-grinding step c).

26. Process according to any of aspects 21 to 25, wherein that the removal step e) is carried out by using a centrifuge, at least one sieve or a disc separator or mixtures thereof for removing >90 wt.-% of particles with a diameter >100 μm and >70 wt. % of particles with a diameter >20 μm, preferably for removing essentially all particles with a diameter >100 μm and >90 wt.-% of particles with a diameter >20 μm, based on the weight of at least one wet ground calcium carbonate comprising material.

27. Process according to any of aspects 21 to 26, wherein step f) of storing the aqueous suspension is carried out at a temperature of from 75 to 130° C. and most preferably from 80 to 95° C., and/or for a period of time of 0.1 to 7 hours, preferably 0.5 to 3.5 hours, more preferably 0.75 to 2.5 hours and most preferably 1 to 2 hours.

28. Process according to any of aspects 21 to 27, wherein the aqueous suspension stored in step f) has solids content of from 5.0 wt.-% to 60.0 wt.-%, preferably from 10.0 wt.-% to 55.0 wt.-%, more preferably from 15.0 wt.-% to 50.0 wt.-% and most preferably from 20.0 wt.-% to 50.0 wt.-%, based on the total weight of the aqueous suspension.

29. Process according to any of aspects 21 to 28, wherein the ratio of particles having an average particle size $d_{80}$ value to particles having an average particle size $d_{20}$ value $[d_{80}/d_{20}]$ of the at least one calcium carbonate-comprising material obtained after storing step f) is in the range from 1.7 to 3.5, preferably from 2.2 to 3.4.

30. Process according to any of aspects 21 to 29, wherein the process further comprises step g) of dewatering and optionally drying the aqueous suspension obtained in step e) to remove at least a portion of water to obtain a partially dewatered calcium carbonate-comprising material or to obtain a dried calcium carbonate-comprising material.

31. Process according to aspect 30, wherein the material obtained after step f) or step g) is deagglomerated, preferably in a pin-mill.

32. Process according to aspect 30 or 31, wherein the obtained material is heated to a temperature in the range from 60 to 150° C., preferably 70 to 130° C. and most preferably 80 to 110° C. to obtain a material with a total moisture content in the range from 0.05 to 0.2 wt.-%, preferably 0.01 to 0.1 wt.-% based on the total weight of the calcium carbonate-comprising material.

33. Process according to any of aspects 31 to 32, wherein,
   c) the partially dewatered calcium carbonate-comprising material is treated after dewatering step g) with at least one dispersing agent and re-diluted to obtain an aqueous suspension comprising a dispersed calcium carbonate-comprising material, and/or d) the partially dewatered calcium carbonate-comprising material and/or the dried calcium carbonate-comprising material is treated before or after dewatering or drying step g) with at least one saturated aliphatic linear or branched carboxylic acid and/or with at least one mono-substituted succinic anhydride and/or at least one mono-substituted succinic acid and/or salty reaction product(s) and/or with at least one phosphoric acid ester blend of one or more phosphoric acid mono-ester and/or reaction products thereof and one or more phosphoric acid di-ester and/or reaction products thereof to obtain a hydrophobized calcium carbonate-comprising material.

34. Process according to any of aspects 21 to 30, wherein the at least one calcium carbonate-comprising material obtained in step f) has
- a) a BET specific surface area of $\leq 15.0$ m$^2$/g, preferably in the range from 1.0 to 15.0 m$^2$/g, more preferably from 2.0 to 14.0 m$^2$/g, and most preferably from 2.5 to 13.0 m$^2$/g, and/or
- b) a lower ratio of particles having an average particle size $d_{80}$ value to particles having an average particle size $d_{20}$ value $[d_{80}/d_{20}]$ than a calcium carbonate-comprising material that is obtained in an identical manner but without contacting step d) and/or storing step f).

35. Process according to any of aspects 31 to 34, wherein the at least one calcium carbonate-comprising material obtained in step g) has
- a) a BET specific surface area of $\leq 15.0$ m$^2$/g, preferably in the range from 1.0 to 15.0 m$^2$/g, more preferably from 2.0 to 14.0 m$^2$/g, and most preferably from 2.5 to 13.0 m$^2$/g, and/or
- b) a lower ratio of particles having an average particle size $d_{80}$ value to particles having an average particle size $d_{20}$ value $[d_{80}/d_{20}]$ than a calcium carbonate-comprising material that is obtained in an identical manner but without storing step f).

Furthermore, reference is made to the detailed description of process steps a), c), e), f) and g) provided herein above with respect to the process according to the first aspect of the present invention. It is emphasized that said detailed description of said process steps and the further preferred embodiments described therein also apply to the process according to the 21th aspect of the present invention.

In the following, reference is made to the contemplated use of the calcium carbonate comprising material which is obtainable by the inventive process according the first aspect of the present invention as well as by the process according to the third and 21th aspect of the present invention.

The calcium carbonate-comprising material thus obtained, either in form of an aqueous suspension comprising the calcium carbonate-comprising material and/or in form of a partially dewatered or dried calcium carbonate-comprising material, and optionally further treated with at least one dispersing agent and re-diluted to obtain an aqueous suspension and/or treated with at least one saturated aliphatic linear or branched carboxylic acid, can be used in paper and board applications, in cosmetics, in caulks and sealants, in adhesives, in paints and coatings, in fibre applications, in plastics applications or for the replacement of PCC in general.

In another embodiment the products obtained by the process according to the present invention are used in paper and board applications, in cosmetics, in caulks and sealants, in adhesives, in paints and coatings, in fibre applications, in plastics applications or for the replacement of PCC in general. For paper and board applications dewatering and optional drying step g) may not be carried out, or the material is only party dewatered, since for these typically slurries of the calcium carbonate-comprising material are used. For all other applications as given above it is preferred to carry out dewatering and optional drying step g).

The use of the products manufactured by the process according to the present invention in plastic applications is preferred. A suitable polymer material for said plastic applications comprises homopolymers, copolymers, such as, for example, block, graft, random and alternating copolymers, heterophasic copolymers and random heterophasic copolymers as well as polymer blends, modifications, or mixtures thereof. The term polymer material as used herein may likewise comprise recycled polymer materials. The content of recycled polymers in the polymer material may be in the range from 0.01 to 100 wt.-%.

The polymer material may be a neat or virgin polymer material or may already comprise a filler before the formation of the polymer composition.

According to one embodiment, the mineral filler material present in the polymer material is identical to the mineral filler mineral material provided according to the inventive process.

According to another embodiment, the filler present in the polymer is different from the mineral filler material provided according to the inventive process.

The polymer optionally may comprise one or more additives which are well known to the skilled person.

Such additives comprise, without being limited to, UV-absorbers, light stabilizers, processing stabilizers, antioxidants, heat stabilizers, nucleating agents, metal deactivators, impact modifiers, plasticizers, lubricants, rheology modifiers, processing aids, pigments, dyes, optical brighteners, antimicrobials, antistatic agents, slip agents, anti block agents, coupling agents, dispersants, compatibilizers, oxygen scavengers, acid scavengers, markers, antifogging agents, surface modifiers, flame retardants, blowing agents, smoke suppressors, reinforcement agents, such as glass fibres, carbon fibres and/or glass bubbles, or mixtures of the foregoing additives.

Preferably, the additives are selected from the class of acid scavengers based on salts of long chain carboxylic acids, such as calcium stearate, magnesium stearate, zinc stearate, and calcium lactate, or may be hydrotalcite, from the class of stabilizers based on phenolic antioxidants, benzofuranones, hydroxylamines, nitrones, thiosynergists, and phosphites/phosphonites, from the class of light stabilizers based on hindered amines (HALS), from the class of metal deactivators, from the class of dispersing agents, coupling agents, or compatibilizers, or a mixture of any of the foregoing additives.

Suitable phenolic antioxidants are, for example: Octadecyl-3-(3,5-di-tert-butyl-4-hydroxyphenyl)propanoate, pentaerythritol-tetrakis[3-(3,5-di-tert-buty 1-4-hydro-xyphenyl) propanoate, tris(3,5-di-tert-butyl-4-hydroxyphenyl) isocyanurate, 1,3,5-trimethyl-2,4,6-tris(3,5-di-tert-butyl-4-hydroxybenzyl)benzene, triethyleneglycol-bis[3-(3-tert-butyl-4-hydroxy-5-methylphenyl)propanoate, N,N'-hexane-1,6-diyl-bis[3-(3,5-di-tert-butyl-4-hydroxyphenyl) propanamide.

Suitable phosphites/phosphonites are, for example: Tris-(2,4-di-tert-butylphenyl)-phosphite, 3,9-bis(2,4-di-tert-butylphenoxy)-2,4,8,10-tetraoxa-3,9-diphospha-spiro[5.5]undecene, tetrakis(2,4-di-tert-butylphenyl)[1,1-biphenyl]-4,4'-diylbisphosphonite.

Suitable sterically hindered amines are, for example: 1,1-Bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)-n-butyl-3,5-di-tert-butyl-4-hydroxybenzylmalonate, the condensation product of 1-(2-hydroxyethyl)-2,2,6,6-tetramethyl-4-hydroxypiperidin and succinic acid, linear or cyclic condensation products of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinon), 4-benzoyl-2,2,6,6-tetramethylpiperidine, 4-stearyloxy-2,2,6,6-tetramethylpiperidine, linear or cyclic condensation products of N,N'-bis(2,2,6,6-tetramethyl-4-piperidyl)hexamethylenediamine and 4-morpholino-2,6-dichloro-1,3,5-triazine, the reaction product of 7,7,9,9-tetramethyl-2-cycloundecyl-1-oxa-3,8-diaza-4-oxospiro[4.5]decene and epichlorohydrine.

Suitable dispersants are, for example: Polyacrylates, such as copolymers with long side chains, and polyacrylate block copolymers; alkylamides, such as N,N'-1,2-ethanediylbisoctadecaneamide; sorbitan esters, such as monostearylsorbitan ester; titanates and zirconates; reactive copolymers, such as polypropylene-acrylic acid copolymer; polypropylene-maleic anhydride copolymer; polyethylene-glycidylmethacrylate copolymer; polystyrol-maleic anhydride-polysiloxane alternating copolymer, such as dimethyl silanediol-ethyleneoxide copolymer; polyphenylsiloxan copolymer; amphiphilic copolymers, such as polyethylene-polyethyleneoxide block copolymer; and dendrimers, such as hydroxy containing dendrimers.

A suitable metal deactivator may be, for example, N,N'-bis(3,5-di-tert-butyl-4-hydroxyphenylpropionyl)hydrazine. According to another embodiment, the metal deactivator may be selected from one or more of the following structures:

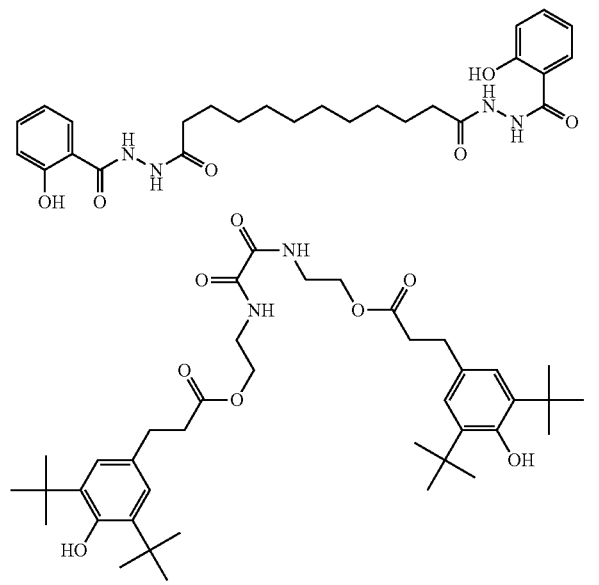

According to one embodiment the polymer material comprises a thermoplastic resin, wherein the thermoplastic resin preferably comprises a polyolefin.

Suitable thermoplastic resins may comprise without being limited to:

a) Polymers from olefins and diolefins, for example, polyethylenes (LDPE, LLDPE, VLDPE, ULDPE, MDPE, HDPE, UHMWPE), polypropylene, polyisobutylene, poly-4-methyl-pentene-1, polybutadiene, polyisoprene, polycyclooctene, as well random or block copolymers, such as ethylene/but-1-ene copolymers, ethylene-hexene copolymers, ethylene-methylpentene copolymers, ethylene-octene copolymers, polypropylene-polyethylene (EP), EPM, EPDM, ethylene-vinylacetate (EVA), and ethylene-acrylic ester copolymers b) Polystyrene, polymethylstyrene, styrene-butadiene copolymers (SB), styrene-butadiene-styrene (SBS) and its hydrogenated polymer (SEBS), Styrene-isoprene, styrene-isoprene-styrene (SIS), styrene-butadiene-acrylnitrile (ABS), styrene-acrylnitrile-acrylate (ASA), styrene-maleic anhydride, and grafted polymers, for example, styrene-grafted butadiene, maleic acid anhydride-grafted SBS, or grafted polymers from methylmethacrylate, styrene-butadiene and ABS (MABS)

c) Halogen containing polymers such as polyvinylchloride, polychloroprene, polyvinylidenchloride, chlorinated polyethylene, or polytetrafluoroethylene, d) Polymers from unsaturated esters such as polyacrylates, or polymethacrylates, for example, polymethylmethacrylate, polyacrylonitrile, polyacrylamide, polybutylacrylate, e) Polymers derived from unsaturated alcohols such as polyvinylalcohol, polyvinylacetate, or polyvinylbutyral (PVB)

f) Polyacetales, for example, polyoxymethylene and copolymers thereof g) Polyphenyleneoxide as well as polystyrene or polyamide blends thereof h) Polyurethanes (PU), in particular linear polyurethanes (TPU)

i) Polyamides (PA) including homo- and copolyamides, such as PA 6, PA 6.6, PA 6/66, PA 6.10, PA 4.6, PA 4.10, PA 6.12, PA 12.12, PA 11, PA 12 as well as partially aromatic polyamides (e.g. polyphthalamides like PA 10T/6T, PA 6T/6I, PA 6T/66) and blends or mixtures thereof, (nomenclature according to ISO 1874-1:2010)

j) Polyimides, polyamidimides, polyetherimides, polyketones, polysulfones, polyethersulfones, and polyphenylensulfides k) Polyethyleneterephthalate (PET), polybutyleneterephthalate (PBT), polypropyleneterephthalate, polyethylenenaphthylate, l) Polycarbonates, m) Cellulose derivatives, such as cellulose nitrate, cellulose acetate, or cellulose propionate n) Partially or fully bio-based polymers derived from renewable biomass sources, such as vegetable fats and oils, corn starch, pea starch, or microbiota, aliphatic biopolyesters, such as polyhydroxyalkanoates (PHA), polyhydroxybutyrate (PHB), polyhydroxyvalerate (PHV), polyhydroxyhexanoate (PHH), or polyesters such as polylactic acid (PLA), o) Blends, mixtures, alloys and combinations comprising at least one of the above polymers According to one embodiment, the polyolefin is selected from the group of homo- and/or copolymers of polyethylene, homo- and/or copolymers of polypropylene, homo- and/or copolymers of polybutylene, or mixtures thereof.

According to a particularly preferred embodiment, the polymer comprises a low density polyethylene (LDPE) and/or a linear low density polyethylene (LLDPE).

According to another particularly preferred embodiment, the polymer is a low density polyethylene (LDPE) and/or a linear low density polyethylene (LLDPE).

According to yet another particularly preferred embodiment the polymer is LDPE having a density ranging from 0.910 to 0.940 g/cm$^3$, LLDPE having a density ranging from 0.915 to 0.925 g/cm$^3$, VLDPE having a density ranging from 0.880 to 0.915 g/cm$^3$, or a mixture thereof.

According to one embodiment of the present invention the use of the products obtained by the inventive processes is preferred in plastic applications such as granulates, pipes, technical profiles, wall panels, ceiling panels, cladding panels, wire or cable insulations, films (e.g. blown films and breathable films, biaxially oriented films, preferably polyethylenterephthalate-, polyamide-, polyethylene- or polypropylene-comprising films), sheets or fibres.

In the art, many methods for the manufacture of polymer products are known. These methods include, without being limited to, melt processing techniques, for example, profile extrusion (for pipes, sheets and hollow sheets), cable extrusion, film extrusion (for cast films and blown films), molding (e.g., injection molding, rotomolding, blow molding and thermoforming), fibre spinning (e.g., melt spinning, wet spinning, dry spinning and structural fibres), co-kneading and pultrusion. The final articles may provide mono-layer or multi-layer structures.

According to one embodiment of the present invention the products obtained by the inventive process are used for various shaped articles. Examples include flexible packaging for industrial and consumer applications, including roll stocks, bags, pouches, labels, wraps, liddings, shrink sleeves and stretch films; rigid packaging for industrial and consumer applications including plastic bottles, cups and containers; building and construction materials, including pipes and conduits, cladding and profiles, insulations, seals and gaskets, geotextiles; agriculture and horticulture materials including greenhouse materials, mulch films, tunnel, silage, bale wraps, boxes and crates; transportation and automotive applications including interior parts, such as instrument and door panels, consoles, pillars and seating; exterior parts, such as bumper fascia, fenders, tailgates as well as under the hood applications including air ducts, air intake manifolds, radiators and cooling hoses; electrical and electronic applications including CD players, DVD systems, personal computers and TV sets, notebooks, tablets, smartphones, cookers, refrigerators and freezers, washing machines, dishwashers, tools and office equipment; medical and health applications including disposable caps, gowns, masks, scrub suits and shoe covers, drapes, wraps and packs, sponges, dressings and wipes, bed linen, contamination control gowns, examination gowns, lab coats, isolation gowns, diagnostic medical machinery and medical devices; personal care products including absorbent hygiene products (AHP), baby diapers, feminine hygiene products and adult incontinence products, wipes, skin care products, depilatory strips; household and furniture products, including wood composites, decorative foils, floor coverings, flooring, kitchen ware, cleaners, pet care, lawn and garden articles; toys, sports and leisure articles including playhouses, building kits, play vehicles, sports and fitness devices, shoes, clothing and sportswear, safety equipment (helmets, kneepads), sports equipment, and suit cases.

In one embodiment the products obtained by the inventive process are used in PVC-applications like window profiles, pipes, technical profiles such as cable- or wire conducts, wall-, ceiling-, or cladding panels, wire insulations, fibres and non-wovens.

One preferred application of the products obtained by the process according to the invention in the field of moisture curing adhesives is their use for structural bonding and flooring applications including parquet adhesives. Due to their high fineness and low moisture pick-up the products manufactured according to the inventive products are very well suited for these applications. Satisfactory curing occurs by reaction of the adhesive by reaction with moisture from the ambient air, therefore it is important that the filler material does not bring additional water into the system.

The following examples may additionally illustrate the invention, but are not meant to restrict the invention to the exemplified embodiments. The examples below show the good characteristics such as particle size distribution and BET specific surface area of the at least one calcium carbonate-containing material prepared according to the present invention as well as their superior properties in selected applications.

EXAMPLES

Measurement Methods

The following measurement methods are used to evaluate the parameters given in the examples and claims.

Brookfield Viscosity

The Brookfield-viscosity of a slurry was determined with a Brookfield Viscometer type RVT equipped with a LV-3 spindle at a speed of 100 rpm and room temperature (20±3° C.).

BET Specific Surface Area of a Material

The BET specific surface area is measured via the BET method according to ISO 4652 using nitrogen, following conditioning of the sample by heating at 250° C. for a period of 30 minutes. Prior to such measurements, the sample is filtered, rinsed and dried at 110° C. in an oven for at least 12 hours.

Particle Size Distribution (Mass % Particles with a Size <X) and Weight Median Particle Size ($d_{50}$) of a Particulate Material Throughout the present invention, $d_{50}$ is the weight median particle diameter by weight, i.e. representing the particle size so that 50 wt.-% of the particles are coarser or finer.

The average weight median particle diameter of the final products was measured using the sedimentation method. Particle mass was measured directly via X-ray absorption. The sedimentation method measures the gravity-induced settling rates of different size particles in a liquid with known properties. The measurement is made with a Sedigraph™ III Plus of Micromeritics Instrument Corporation. The method and the instrument are known to the skilled person and are commonly used to determine grain size of fillers and pigments. The measurement was carried out in an aqueous solution of 0.1 wt.-% sodium pyrophosphate-solution ($Na_4P_2O_7$). The samples were dispersed using a high speed stirrer and supersonic.

The average volume defined particle size and the average particle size volume distribution of the starting materials are determined via laser diffraction, i.e. the light from a laser passes though a suspension and the particle size distribution is calculated from the resulting diffraction pattern. For samples wherein all particles have the same density, then the volume and mass particle size distributions are the same.

The measurement is made with a CILAS 920 particle-size-analyzer of CILAS, Orleans, France.

pH of an Aqueous Suspension

The pH of the aqueous suspension is measured using a standard pH-meter at approximately 25° C.

Solids Content of an Aqueous Suspension

The suspension solids content (also known as "dry weight") is determined using a Moisture Analyser HR73 commercialized by Mettler-Toledo HB43 with the following settings: temperature of 160° C., automatic switch off 3, standard drying, 5-20 g of suspension.

d/d

The term "d/d" refers to the dry amount based on the dry amount of the solid material.

Ash Content

The ash content test was performed by burning 5 to 30 g of the corresponding polymer composition at 570° C. for 120 minutes.

Filter Pressure Value (FPV)

The filter pressure test was performed on a commercially available Collin Pressure Filter Test Teach-Line FT-E20T-IS. The test method was performed in agreement with European Standard EN 13900-5 with each of the corresponding polymer compositions (16 g effective calcium carbonate per 200 g of final sample, diluent: LLDPE ExxonMobil LL 1001 VX) using a 14 µm type 30 filter (GKD Gebr. Kufferath AG, Duren, Germany), wherein no melt pump was used, the extruder speed was kept at 100 rpm, and wherein the melt temperature was 225 to 230° C. (temperature setting: 190° C./210° C./230° C./230° C./230° C.).

Yield Stress

Yield stress determination was performed according to ISO 527-3. The film specimen width was 15 mm and the testing length 5 cm.

Yield Elongation

Yield stress determination was performed according to ISO 527-3. The film specimen width was 15 mm and the testing length 5 cm.

Tensile E-Modulus

Yield stress determination was performed according to ISO 527-3. The film specimen width was 15 mm and the testing length 5 cm. The E-modulus corresponded to the inclination of the tensile test curve between the points at 0.02% and 2% of elongation.

Visual Evaluation of the Blown Film

Film samples have been put under a light microscope. Calcium carbonate agglomerates appear black upon illumination from below and white upon illumination from above. The evaluation "good" means that no pinholes can be observed in the film.

Visual Evaluation of the Breathable Film

The evaluation is done visually during the processing of the visual film without any auxiliary means for enlargement, "ok" means that no holes, no pineholes, and no stripes are observed.

Tear Propagation Resistance

Determination was performed according to ISO 6383.

Dart Drop Test

Measurement was performed according to ASTMD 1709A.

Water Vapour Transmission Rate (WVTR)

The WVTR value of the breathable films was measured with a Lyssy L80-5000 (PBI-Dansensor A/S, Denmark) measuring device according to ASTM E398.

Hydrostatic Pressure Test

The hydrostatic pressure test has been carried out according to a procedure which is equivalent to AATCC Test Method 127-2013, WSP 80.6 and ISO 811. A film sample (test area=10 cm$^2$) was mounted to form a cover on the test head reservoir. This film sample was subjected to a standardized water pressure, increased at a constant rate until leakage appears on the outer surface of the film, or water burst occurs as a result of film failure (pressure rate gradient=100 mbar/min.). Water pressure was measured as the hydrostatic head height reached at the first sign of leakage in three separate areas of the film sample or when burst occurs. The head height results were recorded in centimetres or millibars of water pressure on the specimen. A higher value indicated greater resistance to water penetration. The TEXTEST FX-3000, Hydrostatic Head Tester (Textest AG, Switzerland), was used for the hydrostatic pressure measurements.

Charpy Impact Strength

Charpy notched impact strength was measured according to ISO 179-1:2000 according to conditions 1eA on V-notched extruded samples which were cut out of the extrudate in machine direction. Measuring conditions: 23° C.±2° C. and 50%±10% relative humidity. The test specimens were prepared by extrusion as described in ISO 3167 Typ A.

Surface Gloss

The surface gloss was measured with a Byk Spectro Guide Sphere Gloss at an angle of 60° from the plane surface according to ISO 2813:1994. The gloss value is determined by calculating the average value of n measurement. In the present set up n=10.

L*a*b*

Determination was performed according to DIN 6174.

Moisture Pick-Up Susceptibility

The moisture pick up susceptibility has been determined in mg moisture/g after exposure to an atmosphere of 10 and 85% relative humidity, respectively, for each 2.5 h at a temperature of +23° C. (±2° C.). For this purpose, the sample has been first kept at an atmosphere of 10% relative humidity for 2.5 h, then the atmosphere has been changed to 85% relative humidity at which the sample is kept for another 2.5 hours. The weight increase between 10 and 85% relative humidity has been used to calculate the moisture pick-up in mg moisture/g of sample.

Tackfreetime

The tack free time has been determined according to ASTM C679-03(2009)e1. The sealant/adhesive is applied out of a cartridge (3 mm opening) as a 20 cm long string on a plastic film. Every 5 minutes a piece of plastic film (3 cm times 3 cm) is placed on the string of adhesives with soft pressure for 10 seconds. Then the piece of plastic film is removed. If there is no sealant/adhesive residue left on the plastic film, the tack free time is reached. The test is repeated every 5 minutes until tack free time is reached.

Bond Strength and Maximum Force

The lap shear test for determining the bond strength has been carried out according to ISO 6237 (2003): standard and is using wood substrates to produce lap shear test pieces. The adhesive is applied with a thickness of 1 mm on an area of 25 mm times 25 mm.

The maximum force is the force that was applied by the measurement device to destroy the lap shear test piece.

Tensile Strength at Break

The tensile strength at break is the force per square mm that is needed to destroy Dumbel test pieces (ISO 37).

Elongation at Break

The elongation at break is the maximum elongation which was achieved with the Dumbell test pieces (ISO 37) at the point when the test piece broke.

Rotational Viscosity

The viscosity has been measured with a Paar Physica MCR 301 with a plate-plate set up (1 mm gap) with a rotation measurement set up. The viscosity has been measured at different shear rates between 0.1 and 50 Pa s.

Sodium Content

The sodium content has been determined by ion chromatography on a Metrohm Compact IC 882 plus.

Sodium Hydroxide Content

After the filter cakes were dried and de-agglomerated, they were analysed via XRD for detection of cristallized NaOH. No Na-bearing phase was found in the dried samples so that NaOH does not crystallize during filter cake drying, but is rather present as an amorphous phase. In the trials the remaining NaOH was calculated after determination of the sodium content.

Preparation of Calcium Carbonate-Comprising Material

Example A (Comparative Example)

A slurry of dispersant-free wet-ground natural calcium carbonate (obtained by processing of marble from Omya's quarry in Gummern, Austria) featuring an average particle size of about 19 μm (measured on CILAS 920 from Cilas S.A.) was adjusted to a solids content of 45.8 wt.-% and adjusted to a temperature of 40° C.

The resulting suspension was then further wet-ground in a vertical agitated bead mill with 1.96 m$^3$ net volume (empty grinding chamber) that was filled with 1 500 kg $ZrO_2$/$Al_2O_3$-based grinding beads having a diameter in the range from 1.8 to 2.0 mm and a bulk density of 2 400 kg/m$^3$. Volumetric feed rate and rotational speed of the mixing shaft were adjusted to obtain a target average particle size after the mill of about 1.8 μm (measured on Sedigraph III Plus from Micromeritics). Shaft rotational speed at these operating conditions was 220 min$^{-1}$. Power uptake was 158 kW at 5.0 m$^3$/h feed rate, corresponding to a specific grinding energy of 49 kWh/dry metric ton.

The slurry discharged from the mill was then transferred to a decanter centrifuge (SC3043, supplied by Bird-Humboldt) for degritting and to remove coarse particles contained in the slurry. Drum diameter of the centrifuge was 465 mm, pool depth 320 mm and cone angle 10°. Feed rate to the centrifuge was 5.0 m$^3$/h. Rotational speed was 1 600 min$^{-1}$ and differential speed set to 50 min$^{-1}$, resulting in a torque of 12%.

The product discharged from the degritting centrifuge was recovered as an aqueous slurry of ground calcium carbonate. Physical data are given in Table 1a, column A. PSD Sedigraph is given in FIG. 1.

Example B (Invention)

A slurry of dispersant-free wet-ground natural calcium carbonate (obtained by processing of marble from Omya's quarry in Gummern, Austria) featuring an average particle size of about 17 μm (measured on CILAS 920 from Cilas S.A.) was adjusted to a solids content of 44.5 wt.-% and adjusted to a temperature of 40° C.

The resulting suspension was then further wet-ground in a vertical agitated bead mill with 1.96 m$^3$ net volume (empty grinding chamber) that was filled with 3 000 kg $ZrO_2$/$SiO_2$-based grinding beads having a diameter in the range from 0.7 to 1.4 mm and a bulk density of 2 300 kg/m$^3$. Volumetric feed rate and rotational speed of the mixing shaft were adjusted to obtain a target average particle size after the mill of about 1.0 μm (measured on Sedigraph III Plus from Micromeritics). Shaft rotational speed at these operating conditions was 190 min$^{-1}$. Power uptake was 268 kW at 4.0 m$^3$/h feed rate, corresponding to a specific grinding energy of 109 kWh/dry metric ton. To the bottom of the bead mill 5.2 m$^3$/h of 20° C. tap water was added for dilution.

The slurry discharged from the mill was then transferred to a decanter centrifuge (SC3043, supplied by Bird-Humboldt) for degritting and to remove coarse particles contained in the slurry. Drum diameter of the centrifuge was 465 mm, pool depth 320 mm and cone angle 10°. Feed rate to the centrifuge was 9.2 m$^3$/h. Rotational speed was 1800 min$^{-1}$ and differential speed set to 60 min$^{-1}$, resulting in a torque of 13%.

The product discharged from the degritting centrifuge was transferred to an agitated autoclave vessel and 0.5% (calculated as active on dry matter $CaCO_3$) of a 48 wt-% NaOH solution was added. The reaction mixture was then heated and stored at a temperature of 115° C. under agitation for 120 minutes. After 120 min, the slurry was cooled to 25° C. and recovered as an aqueous slurry of ground calcium carbonate. Physical data are given in Table 1a, column B. PSD Sedigraph is given in FIG. 1.

Example C (Comparative Example)

A slurry of dispersant-free wet-ground natural calcium carbonate (obtained by processing of marble from Omya's quarry in Gummern, Austria) featuring an average particle size of about 31 μm (measured on CILAS 920 from Cilas S.A.) was adjusted to a solids content of 45.2 wt.-% and adjusted to a temperature of 40° C.

The resulting suspension was then further wet-ground in a vertical agitated bead mill with 1.96 m$^3$ net volume of the empty grinding chamber and that was filled with 4 000 kg $ZrO_2$-based grinding beads with a diameter in the range from 0.9 to 1.1 mm and a bulk density of 3800 kg/m$^3$. Volumetric feed rate and rotational speed of the mixing shaft were adjusted to obtain a target average particle size after the mill of about 60%<1 μm (measured on Sedigraph III Plus from Micromeritics). Shaft rotational speed at these operating conditions was 320 min$^{-1}$. Power uptake was 843 kW at 5.6 m$^3$/h feed rate, corresponding to a specific grinding energy of 241 kWh/dry metric ton. To the bottom of the bead mill 6.4 m$^3$/h of 20° C. tap water was added for dilution.

The slurry discharged from the mill was then transferred to a decanter centrifuge (SC3043, supplied by Bird-Humboldt) for degritting and to remove coarse particles contained in the slurry. Drum diameter of the centrifuge was 465 mm, pool depth 320 mm and cone angle 10°. Feed rate to the centrifuge was 12.0 m$^3$/h. Rotational speed was 1 800 min$^{-1}$ and differential speed set to 60 min$^{-1}$, resulting in a torque of 15%.

The product discharged from the degritting centrifuge was recovered as an aqueous slurry of ground calcium carbonate. Physical data are given in Table 1a, column C, PSD Sedigraph is given in FIG. 2.

Example D (Invention)

The aqueous slurry obtained under example C was transferred to an agitated autoclave vessel and 0.5% (calculated as active on dry matter $CaCO_3$) of a 48 wt.-% NaOH solution was added. The reaction mixture was then heated and stored at a temperature of 115° C. under agitation for 120 minutes. After 120 minutes, the slurry was cooled to 25° C. and recovered as an aqueous slurry of ground calcium carbonate. Physical data are given in Table 1a, column D. PSD Sedigraph is given in FIG. 2.

TABLE 1a

| | | Example | | | |
|---|---|---|---|---|---|
| | Unit | A CE | B IE | C CE | D IE |
| NaOH (% active/dry $CaCO_3$) | | 0 | 0.5 | 0 | 0.5 |
| pH before storage | | 8.3 | 12.4 | 8.3 | 12.9 |
| Storage temp. | ° C. | — | 115 | — | 115 |
| Storage after mill | min | — | 120 | — | 120 |
| SSA | m²/g | 5.1 | 3.0 | 7.3 | 4.6 |
| PSD | | | | | |
| <5 μm | wt.-% | 91 | 97 | 98 | 98 |
| <2 μm | wt.-% | 58 | 58 | 84 | 78 |
| <1 μm | wt.-% | 32 | 11 | 57 | 33 |
| <0.5 μm | wt.-% | 15 | 1 | 23 | 5 |
| <0.2 μm | wt.-% | 6 | | 6 | |
| $d_{50}$ | μm | 1.66 | 1.82 | 0.87 | 1.26 |
| $d_{98}$ | μm | 8.20 | 5.70 | 5.00 | 5.20 |
| $d_p$ | μm | 0.44 | 0.72 | 0.30 | 0.48 |
| $\Delta d_{50} d_p$ | % | 280 | 146 | 190 | 163 |
| Steepness factor [$d_{80}/d_{20}$] | | 5.5 | 2.3 | 4.2 | 3.3 |
| Normalized SSA ($SSA/d_{50}$) | $10^6$ m/g | 3.1 | 1.7 | 8.4 | 3.7 |

CE: Comparative Example
IE: Inventive Example.

Further Process Steps

The aqueous slurry obtained in Example D was divided into three parts (Samples D1 to D3) and submitted to further process steps.

Sample D1 started with a $CaCO_3$ slurry of 10 000 g of 25 wt.-% solids content. The slurry was not mechanically dewatered but spray dried at an inlet temperature of 200° C.

Sample D2 started with a $CaCO_3$ slurry of 10 000 g of 25 wt.-% solids content. The slurry was mechanically dewatered to a solids content of 50 wt.-% by using a press filter equipment at a pressure of 2 to 2.5 bar and the obtained cake was dried in an oven at 110° C. During mechanical dewatering, 7 500 g of tap water was removed.

Sample D3 started with a $CaCO_3$ slurry of 10 000 g of 25 wt.-% solids content. The slurry was dewatered by using a press filter equipment at a pressure of 2 to 2.5 bar and the cake was washed out with deionised water. During the first mechanical dewatering step, 2 783 g of tap water were removed in order to obtain a solids content of 47.1 wt.-%. The filter cake was then diluted back with deionised water to a solid content of 26.1 wt.-%. Therefore, 2 679.7 g deionised water were added. Again, the slurry was mechanically dewatered by using the same filter press equipment at a pressure of 2 to 2.5 bar to a solids content of 53.7 wt.-%. Therefore 2760.5 g water were removed. The filter cake was then diluted back with deionised water to a solid content of 26.5 wt.-%. Therefore, 2720.6 g of deionised water were added. And finally the slurry was mechanically dewatered again to a solids content of 54.8 wt.-% by removing 2830 g water. This procedure was repeated two times and the obtained cake after the third dewatering step was dried in an oven at 110° C.

TABLE 1b

| | D1 | D2 | D3 |
|---|---|---|---|
| Moisture pick-up [mg/g] | 10.11 | 1.73 | 0.50 |
| NaOH content [wt.-%][a] | n.d. | 0.40 | 0.06 |
| Sodium content [ppm] | n.d. | 1291 | 193 |

[a] wt.-% based on dry weight of calcium carbonate;
n.d. = not determined.

As can be gathered from Table 1b the washing out of residual base is a very efficient measure for lowering the moisture pick-up of the product obtained after the storing step. The moisture pick-up susceptibility correlates directly with the sodium content and NaOH content in the product.

Applications in Polymers

Example 1: Preparation of Masterbatches in Polyethylene for Blown Films

Masterbatches containing 30 wt.-% LLDPE LL 6101 Series (Exxon Mobil), and 70 wt.-% CC1 (comparative example, ground calcium carbonate, commercially available from Omya International AG, Switzerland, $d_{50}$: 1.7 μm; $d_{98}$: 6 μm, surface-treated with 1 wt.-% stearic acid, commercially available from Sigma-Aldrich, Croda, based on the total weight of the ground calcium carbonate) or CC2 (inventive example, calcium carbonate according to example D and surface-treated with 1 wt.-% stearic acid, based on the total weight of the ground calcium carbonate, commercially available from Sigma-Aldrich, Croda), respectively, were prepared on a Buss kneader (PR 46 from Buss AG, Switzerland). The compositions and filler contents of the prepared masterbatches are compiled in Table 2 below. The precise filler content was determined by the ash content. Furthermore, a filter pressure test was carried out in order to determine the dispersion quality of the filler material product.

TABLE 2

Compositions and properties of prepared masterbatches.

| Masterbatch | Filler | Ash content [wt.-%] | MFI (190° C., 5 kg) ISO 1133 [g/10 min] | FPV at 14 μm [bar/g] |
|---|---|---|---|---|
| MB1 (comparative) | CC1 | 69.1 | 23.4 | 0.6 |
| MB2 (inventive) | CC2 | 69.4 | 23.1 | 1.4 |

The results shown in Table 2 confirm that masterbatches with good quality were produced.

Example 2: Manufacture of Blown Film Samples

A blown film having a filler content of 20 wt.-% was produced using 71.4 wt.-% of LLDPE LL 6101 Series (Exxon Mobil) and 28.6 wt.-% of a masterbatch according to the above examples (BF1=Comparative Example, BF2=Inventive Example). Films were produced on a Dr. Collin blown film extrusion line (60 mm circular die, 1.2 mm die gap, 30 mm screw diameter, L/D ratio=30, screw with mixing element). The films were processed with a BUR (blow up ratio) of 2.2 and the frost line high was kept at 16 cm high (distance from die).

The extruder had the following configuration:

TABLE 3

Extruder configuration.

| | Zone | | | | |
|---|---|---|---|---|---|
| | 1 | 2 | 3 | 4 | 5 |
| T [° C.] | 175 | 195 | 215 | 215 | 215 |

Extruder speed was kept constantly at 60 rpm and the average film grammage was set to 35 g/m² by appropriate adjustment of the line speed. Also the cooling air flow was adjusted accordingly to keep the frost line at the same position.

Material and Mechanical Properties of Blown Film Samples:

TABLE 4

Material and mechanical properties of blown film samples BF1 and BF2.

| Blown film sample | Direction[a] | BF1 | BF2 |
|---|---|---|---|
| Yield stress [N · mm⁻²] | MD | 10.1 | 11.3 |
| | CD | 10.8 | 11.8 |
| Yield elongation [%] | MD | 10.9 | 10.4 |
| | CD | 7.6 | 6.7 |
| Tensile modulus [N · mm⁻²] | MD | 301 | 315 |
| | CD | 349 | 361 |
| Tear propagation resistance [cN] | MD | 650 | 720 |
| | CD | 779 | 798 |
| | Σ | 1429 | 1518 |
| Dart drop fall weight [g] | — | 657 | 675 |
| Visual evaluation of film | — | good | good |
| Ash content [wt.-%] | — | 19.0 | 18.2 |
| Film thickness [μm] | — | 34 | 32 |

MD = machine direction,
CD = cross direction.

As can be gathered from Table 4 the films comprising the filler according to present invention show improved mechanical properties.

Example 3—Preparation of Polyolefin Masterbatches for Breathable Films

The following polyolefins have been used for the preparation of masterbatches.

P1: LLDPE Dowlex 2035 (MFR: 6 g/10 min (190° C., 2.16 kg), density: 0.919 g/cm³ according to technical data sheet), commercially available from The Dow Chemical Company, USA.

P2: LDPE Dow SC 7641 (MFR: 2 g/10 min (190° C., 2.16 kg), density: 0.923 g/cm³ according to technical data sheet), commercially available from The Dow Chemical Company, USA.

Masterbatches containing 45 wt.-% P1, 5 wt.-% P2, and 50 wt.-% CC1 (comparative example, ground calcium carbonate, commercially available from Omya International AG, Switzerland, $d_{50}$: 1.7 μm; $d_{98}$: 6 μm, surface-treated with 1 wt.-% stearic acid, commercially available from Sigma-Aldrich, Croda, based on the total weight of the ground calcium carbonate) or CC2 (inventive, according to example D and coated with 1 wt.-% stearic acid, based on the total weight of the calcium carbonate, commercially available from Sigma-Aldrich, Croda), respectively, were continuously prepared on Buss kneader (PR46 from Buss AG, Switzerland). The compositions and filler contents of the prepared masterbatches are compiled in Table 5 below. The precise filler content was determined by the ash content.

TABLE 5

Compositions and properties of prepared masterbatches.

| Masterbatch | Filler | Ash content [wt.-%] |
|---|---|---|
| MB1 (comparative) | CC1 | 48.9 |
| MB2 (inventive) | CC2 | 49.4 |

Example 4—Preparation of Breathable Films

Breathable films were produced by a pilot-extrusion cast-film line with integrated MDO-II unit (Dr. Collin GmbH, Germany) the extruder temperature settings were 195° C.-210° C.-230° C.-230° C., and the rotation speed of the extruder was approximately 35 rpm using the masterbatches of Example 3. The roller speed of the stretching unit was 135/135%.

The film quality of the obtained breathable films was inspected visually and the films were tested regarding their water vapour transmission rate (WVTR) and their hydrostatic pressure. The results are shown in Table 6 below.

TABLE 6

Compositions and properties of prepared breathable films.

| Sample | Masterbatch | Film quality | WVTR | Hydrostatic pressure |
|---|---|---|---|---|
| 1 (comparative) | MB1 | ok | 3850 g/(m² × day) | 330 mbar |
| 2 (inventive) | MB2 | ok | 4700 g/(m² × day) | 275 mbar |

The results shown in Table 6 confirm that the inventive breathable film has a good quality and breathability, which is superior to the comparative breathable film.

Example 5: Preparation and Testing of PVC-Samples

The components for comparative examples PVC1, as well as inventive examples PVC2 were previously mixed using the usual hot/cold mixing process known to the skilled person, and extruded on a Krauss-Maffei KMD 2-90 profile extrusion line, L/D=22, with counter rotating parallel twin screws, the screws having a diameter of 90 mm each.

TABLE 7

Compositions and properties of prepared PVC compounds.

| | Example | |
|---|---|---|
| | PVC1 | PVC2 |
| PVC resin, K-value 66 (Evipol SH6630) | 100 (phr) | 100 (phr) |

TABLE 7-continued

Compositions and properties of prepared PVC compounds.

|  | Example | |
| --- | --- | --- |
|  | PVC1 | PVC2 |
| Acrylic impact modifier (Paraloid KM370) | 6 (phr) | 6 (phr) |
| Ca—Zn containing stabilizer (Stabilox CZ 2913 GN) | 4.65 (phr) | 4.65 (phr) |
| Titanium dioxide (Kronos 2220) | 3.5 (phr) | 3.5 (phr) |
| $CaCO_3$ according to Example D | 8 (phr) | 0 |
| $CaCO_3{}^{a)}$ | 0 | 8 (phr) |
| Charpy impact strength [kJ/m$^2$] ISO179/1fC | 49.4 | 59.5 |
| Gloss 60° [—] | 50.5 | 52.0 |
| L*-value | 95.2 | 95.3 |
| a*/b*-value | −0.45/3.92 | −0.58/3.54 |

$^{a)}$Ground calcium carbonate, commercially available from Omya AG, Switzerland, particle size $d_{50}$: 0.8 µm; top cut $d_{98}$: 5.0 µm.

TABLE 8

Compositions and properties of prepared PVC compounds.

|  | Example | |
| --- | --- | --- |
|  | PVC1 | PVC2 |
| PVC resin, K-value 66 (Evipol SH6630) | 100 (phr) | 100 (phr) |
| Acrylic impact modifier (Paraloid KM370) | 6 (phr) | 6 (phr) |
| Ca—Zn containing stabilizer (Stabilox CZ 2913 GN) | 4.65 (phr) | 4.65 (phr) |
| Titanium dioxide (Kronos 2220) | 3.5 (phr) | 3.5 (phr) |
| $CaCO_3{}^{a)}$ | 16 (phr) | 0 |
| $CaCO_3$ according to Example D | 0 | 16 (phr) |
| Charpy impact resistance [kJ/m$^2$] ISO179/1fC | 55.2 | 56.9 |
| Gloss 60° [—] | 33.7 | 40.7 |
| L*-value | 95.5 | 95.3 |
| a*/b*-value | −0.22/4.18 | −0.45/4.04 |

$^{a)}$Ground calcium carbonate, commercially available from Omya AG, Switzerland, particle size $d_{50}$: 0.8 µm; top cut $d_{98}$: 5.0 µm.

As can be gathered from the results given in Tables 7 and 8 mechanical and optical properties improve when the inventive products are applied. Particularly noteworthy is the significant improvement of the gloss at higher filler contents (see Table 8).

Example 6: Preparation and Testing of Parquet Adhesives (PA)

For the preparation of the parquet adhesives PA1 and PA2 the base resin, softener and calcium carbonate were added in a planetary mixer and stirred for 30 minutes, at 400 rpm under full vacuum at 65° C. After allowing the resulting mixture to cool to room temperature the remaining components as given in Table 9 were added and stirring was continued for another 5 minutes at 200 rpm under vacuum (413 mbar). Afterwards the planetary mixer was purged with nitrogen and the obtained mixture was filled into a cartridge and was stored for 24 hours at 23° C. and 50% humidity.

TABLE 9

Compositions of prepared parquet adhesives.

|  | Example | |
| --- | --- | --- |
|  | PA1 (comparison) | PA2 (invention) |
| Base resin (Kaneka SAX260) | 246 (g) | 246 (g) |
| Softener (DIUP, Jayflex by Exxon) | 123 (g) | 123 (g) |
| Vinyl silane 1 (Dynasylan VTMO) | 6.0 (g) | 6.0 (g) |
| Aminosilane (Dynassylan AMMO) | 7.5 (g) | 7.5 (g) |
| Hardening catalyst (Neostann S-1) | 2.5 (g) | 2.5 (g) |
| UFPCC | 103 g | 103 g |
| $CaCO_3{}^{a)}$ | 512 (g) | — |
| $CaCO_3$ according to Example D | — | 512 (g) |

$^{a)}$Ground calcium carbonate, commercially available from Omya AG, Switzerland, particle size $d_{50}$: 0.9 µm; top cut $d_{98}$: 5 µm, moisture pick-up: 0.35%.

TABLE 10

Results of application tests, mechanical properties and viscosity.

|  | Example | |
| --- | --- | --- |
|  | PA1 (comparison) | PA2 (invention) |
| Tackfreetime [min] | 50 | 50 |
| Extrusion rate [g/min] | 220 | 280 |
| Bond strength [N/mm$^2$] | 2.10 | 2.53 |
| Maximum force [N] | 1265 | 1515 |
| Modulus 100% [%] | 2.0 | 2.1 |
| Tensile at break | 1.8 | 2.2 |
| Elongation at break [N/mm$^2$] | 145 | 165 |
| η at 0.1 s$^{-1}$ [Pa · s] | 2505 | 2640 |
| η at 1 s$^{-1}$ [Pa · s] | 380 | 400 |
| η at 5 s$^{-1}$ [Pa · s] | 100 | 105 |
| η at 10 s$^{-1}$ [Pa · s] | 65 | 65 |
| η at 50 s$^{-1}$ [Pa · s] | 20 | 25 |

As can be gathered from the results given in Tables 10 mechanical and rheological properties improve when the inventive products are applied.

The invention claimed is:

1. A process for the preparation of an aqueous suspension comprising at least one calcium carbonate-comprising material, the process comprising the following steps:
   a) providing a substantially dispersant-free aqueous suspension of at least one calcium carbonate-comprising material having a weight median particle size diameter $d_{50}$ in the range from 0.5 µm to 50.0 µm,
   b) pre-heating the suspension of step a) to a temperature of from 40 to 95° C. at ambient pressure,
   c) wet-grinding the pre-heated suspension of step b) in at least one grinding step to obtain an aqueous suspension of at least one wet ground calcium carbonate-comprising material in which at least 20.0 wt.-% of the at least one calcium carbonate-comprising material has a weight median particle size diameter of ≤1.0 µm,
   d) contacting the aqueous suspension with at least one base to obtain an aqueous suspension having a pH measured at 25° C. of ≥9.0,
   e) removing at least a part of the particles with a diameter >20 µm in the aqueous suspension of the at least one wet ground calcium carbonate-comprising material, and f) heating, agitating, and storing the aqueous suspension obtained after step d) and step e) at a temperature of from 70 to 140° C. for a period of time of 0.25 to 8 hours, to obtain an aqueous suspension of at least one calcium carbonate-comprising material having a ratio of particles having an average particle size $d_{80}$ value to particles having an average particle size $d_{20}$ value [$d_{80}/d_{20}$] in the range from 1.5 to 4.0.

2. The process according to claim 1, wherein step c) is carried out to obtain an aqueous suspension of at least one wet ground calcium carbonate-comprising material in which at least 30.0 wt.-% of the calcium carbonate material has a weight median particle size diameter of ≤1.0 μm.

3. The process according to claim 1, wherein step c) is carried out to obtain an aqueous suspension of at least one wet ground calcium carbonate-comprising material in which at least 45.0 wt.-% of the calcium carbonate material has a weight median particle size diameter of ≤1.0 μm.

4. The process according to claim 1, wherein the at least one calcium carbonate-comprising material provided in the aqueous suspension of step a) is dolomite and/or a natural ground calcium carbonate (NGCC).

5. The process according to claim 1, wherein the at least one calcium carbonate-comprising material provided in the aqueous suspension of step a) is a natural ground calcium carbonate (NGCC) selected from one or more of marble, limestone, and chalk.

6. The process according to claim 1, wherein the aqueous suspension provided in step a) has a solids content of from 5.0 wt.-% to 60.0 wt.-%, based on the total weight of the aqueous suspension.

7. The process according to claim 1, wherein the aqueous suspension provided in step a) has a solids content of from 10.0 wt.-% to 55.0 wt.-%, based on the total weight of the aqueous suspension.

8. The process according to claim 1, wherein the aqueous suspension of step a) is adjusted in pre-heating step b) to a temperature of from 50 to 95° C. at ambient pressure.

9. The process according to claim 1, wherein the aqueous suspension of step a) is adjusted in pre-heating step b) to a temperature of from 75 to 85° C. at ambient pressure.

10. The process according to claim 1, wherein step d) is carried out after step e) but before step f).

11. The process according to claim 1, wherein step d) is carried out such that the obtained aqueous suspension has a pH measured at 25° C. of from 10.0 to 13.5.

12. The process according to claim 1, wherein step d) is carried out such that the obtained aqueous suspension has a pH measured at 25° C. of from 11.0 to 13.0.

13. The process according to claim 1, wherein the at least one base in step d) is added in an amount of ≥0.05 wt.-%, based on the total dry weight of the calcium carbonate-comprising material.

14. The process according to claim 1, wherein the at least one base in step d) is added in an amount of ≥0.1 wt.-%, based on the total dry weight of the calcium carbonate-comprising material.

15. The process according to claim 1, wherein the at least one base in step d) is added in an amount of from 0.2 to 1.0 wt.-%, based on the total dry weight of the calcium carbonate-comprising material.

16. The process according to claim 1, wherein the at least one base in step d) is at least one alkali metal hydroxide selected from the group consisting of lithium hydroxide, sodium hydroxide, potassium hydroxide, and any mixture thereof, and/or at least one earth alkali metal hydroxide selected from the group consisting of magnesium hydroxide, calcium hydroxide, and any mixture thereof.

17. The process according to claim 1, wherein step c) is carried out at a starting temperature of from 40 to 95° C.

18. The process according to claim 1, wherein step c) is carried out at a starting temperature of from 60 to 80° C.

19. The process according to claim 1, wherein step e) is carried out by using a centrifuge, at least one sieve, a disc separator, or any combination thereof, for removing >90 wt.-% of particles with a diameter >100 μm and >70 wt.-% of particles with a diameter >20 μm, based on the weight of the at least one wet ground calcium carbonate comprising material.

20. The process according to claim 1, wherein step e) is carried out by using a centrifuge, at least one sieve, a disc separator, or any combination thereof, for removing essentially all particles with a diameter >100 μm and >90 wt.-% of particles with a diameter >20 μm, based on the weight of the at least one wet ground calcium carbonate comprising material.

21. The process according to claim 1, wherein step f) is carried out at a temperature of from 80 to 95° C., and/or for a period of time of 0.5 to 3.5 hours.

22. The process according to claim 1, wherein the aqueous suspension stored in step f) has solids content of from 5.0 wt.-% to 60.0 wt.-%, based on the total weight of the aqueous suspension.

23. The process according to claim 1, wherein the aqueous suspension stored in step f) has solids content of from 20.0 wt.-% to 50.0 wt.-%, based on the total weight of the aqueous suspension.

24. The process according to claim 1, wherein the ratio of particles having an average particle size $d_{80}$ value to particles having an average particle size $d_{20}$ value [$d_{80}/d_{20}$] of the at least one calcium carbonate-comprising material obtained after storing step f) is in the range from 1.7 to 3.5.

25. The process according to claim 1, wherein the ratio of particles having an average particle size $d_{80}$ value to particles having an average particle size $d_{20}$ value [$d_{80}/d_{20}$] of the at least one calcium carbonate-comprising material obtained after storing step f) is in the range from 2.2 to 3.4.

26. A process for the preparation of an aqueous suspension comprising at least one calcium carbonate-comprising material, the process comprising the following steps:
   a) providing a substantially dispersant-free aqueous suspension of at least one calcium carbonate-comprising material, and
   b) pre-heating the suspension of step a) to a temperature of from 40 to 95° C. at ambient pressure, and
   c) wet-grinding the pre-heated suspension in at least one grinding step for obtaining an aqueous suspension of at least one wet ground calcium carbonate-comprising material, and
   d) contacting the aqueous suspension with at least one base for obtaining an aqueous suspension having a pH measured at 25° C. of ≥9.0, and
   e) removal of at least a part of the particles with a diameter >20 μm in the aqueous suspension of the at least one wet ground calcium carbonate comprising material,
   f) heating, agitating, and storing the aqueous suspension obtained after removal step e) at a temperature of from 70 to 140° C. for a period of time of 0.25 to 8 hours, for obtaining an aqueous suspension of at least one calcium carbonate-comprising material having a ratio of particles having an average particle size $d_{80}$ value to particles having an average particle size $d_{20}$ value [$d_{80}/d_{20}$] in the range from 1.5 to 4.0, and g) of dewatering, and optionally drying the aqueous suspension obtained in step e) or f) to remove at least a portion of water to obtain a partially dewatered calcium carbonate-comprising material or to obtain a dried calcium carbonate-comprising material.

27. The process according to claim 26, wherein water is added to the partially dewatered calcium carbonate-comprising material obtained after step g) or to the dried calcium carbonate-comprising material to obtain an aqueous suspension and the obtained aqueous suspension is dewatered.

28. The process according to claim 27, wherein the procedure of adding water and dewatering is repeated two times.

29. The process according to claim 26, wherein the material obtained after step f) or step g) is deagglomerated.

30. The process according to claim 26, wherein the obtained material is heated to a temperature in the range from 60 to 150° C., to obtain a material with a total moisture content in the range from 0.05 to 0.2 wt.-%, based on the total weight of the calcium carbonate-comprising material.

31. The process according to claim 26, wherein the obtained material is heated to a temperature in the range from 70 to 130° C., to obtain a material with a total moisture content in the range from 0.01 to 0.1 wt.-%, based on the total weight of the calcium carbonate-comprising material.

32. The process according to claim 26, wherein:
a) the partially dewatered calcium carbonate-comprising material is treated after dewatering step g) with at least one dispersing agent and re-diluted to obtain an aqueous suspension comprising a dispersed calcium carbonate-comprising material, and/or
b) the partially dewatered calcium carbonate-comprising material and/or the dried calcium carbonate-comprising material is treated before or after dewatering or drying step g) with an agent selected from the group consisting at least one saturated aliphatic linear carboxylic acid, at least one saturated aliphatic branched carboxylic acid, at least one mono-substituted succinic anhydride, at least one mono-substituted succinic acid or reaction product thereof, at least one phosphoric acid ester blend of one or more phosphoric acid mono-ester and/or reaction products thereof, and one or more phosphoric acid di-ester and/or reaction products thereof, to obtain a hydrophobized calcium carbonate-comprising material.

33. The process according to claim 1, wherein the at least one calcium carbonate-comprising material obtained in step f) has a BET specific surface area of ≤15.0 m²/g.

34. The process according to claim 1, wherein the at least one calcium carbonate-comprising material obtained in step f) has a BET specific surface area of from 1.0 to 15.0 m²/g.

35. The process according to claim 1, wherein the at least one calcium carbonate-comprising material obtained in step f) has a lower ratio of particles having an average particle size $d_{80}$ value to particles having an average particle size $d_{20}$ value $[d_{80}/d_{20}]$ than a calcium carbonate-comprising material that is obtained in an identical manner but without pre-heating step b) and contacting step d) and/or storing step f).

36. The process according to claim 26, wherein the at least one calcium carbonate-comprising material obtained in step g) has a BET specific surface area of ≤15.0 m²/g.

37. The process according to claim 26, wherein the at least one calcium carbonate-comprising material obtained in step g) has a BET specific surface area of from 1.0 to 15.0 m²/g.

38. The process according to claim 26, wherein the at least one calcium carbonate-comprising material obtained in step g) has a lower ratio of particles having an average particle size $d_{80}$ value to particles having an average particle size $d_{20}$ value $[d_{80}/d_{20}]$ than a calcium carbonate-comprising material that is obtained in an identical manner but without pre-heating step b) and contacting step d) and/or storing step f).

39. A process for the preparation of an aqueous suspension comprising at least one calcium carbonate-comprising material, the process comprising the following steps:
a) providing a substantially dispersant-free aqueous suspension of at least one calcium carbonate-comprising material, and
b) pre-heating the suspension of step a) to a temperature of from 40 to 95° C. at ambient pressure, and
c) wet-grinding the pre-heated suspension in at least one grinding step for obtaining an aqueous suspension of at least one wet ground calcium carbonate-comprising material, and
d) contacting the aqueous suspension with at least one base for obtaining an aqueous suspension having a pH measured at 25° C. of ≥9.0, and
e) removal of at least a part of the particles with a diameter >20 μm in the aqueous suspension of the at least one wet ground calcium carbonate comprising material, and
f) heating, agitating, and storing the aqueous suspension obtained after removal step e) at a temperature of from 70 to 140° C. for a period of time of 0.25 to 8 hours, for obtaining an aqueous suspension of at least one calcium carbonate-comprising material having a ratio of particles having an average particle size $d_{80}$ value to particles having an average particle size $d_{20}$ value $[d_{80}/d_{20}]$ in the range from 1.5 to 4.0.

* * * * *